(12) United States Patent
Hong et al.

(10) Patent No.: US 9,238,820 B2
(45) Date of Patent: Jan. 19, 2016

(54) MOLECULAR ENGINEERING OF A FLORAL INDUCER FOR CROP IMPROVEMENT

(75) Inventors: Yiguo Hong, Stratford-Upon-Avon (GB); Steve Jackson, Gibbet Hill (GB); Chunyang Li, Chengdu (CN)

(73) Assignees: THE UNIVERSITY OF WARWICK, Coventry (GB); PLANT BIOSCIENCE LIMITED, Norwick, Norfolk (GB)

( * ) Notice: Subject to any disclaimer, the term of this patent is extended or adjusted under 35 U.S.C. 154(b) by 530 days.

(21) Appl. No.: 13/564,936

(22) Filed: Aug. 2, 2012

(65) Prior Publication Data

US 2013/0081151 A1    Mar. 28, 2013

Related U.S. Application Data

(63) Continuation-in-part of application No. PCT/GB2011/050440, filed on Mar. 7, 2011.

(30) Foreign Application Priority Data

Mar. 5, 2010   (GB) .................................. 1003702.6

(51) Int. Cl.
  *C12N 15/82*   (2006.01)
  *C07K 14/415*   (2006.01)
(52) U.S. Cl.
  CPC .......... *C12N 15/8261* (2013.01); *C07K 14/415* (2013.01); *C12N 15/827* (2013.01)
(58) Field of Classification Search
  None
  See application file for complete search history.

(56) References Cited

U.S. PATENT DOCUMENTS

2007/0192904 A1*  8/2007  Kardailsky et al. ........... 800/287

FOREIGN PATENT DOCUMENTS

| WO | WO 99/53070 | 10/1999 |
| WO | WO 2004/067723 | 8/2004 |

OTHER PUBLICATIONS

Kardailsky et al.(Science 1999, Dec. 3, vol. 286 1962-1965).*
Koornneef et al. (Mol Gen Genet, 1991, 229:57-66).*
Tamaki et al. (Science vol. 316 May 18, 2007 pp. 1033-1035).*
Morrison et al. (Current Opinion in Chemical Biology vol. 5, Issue 3, Jun. 1, 2001, pp. 302-307).*
Hanzawa, et al., A Single Amino Acid Converts A Repressor to an Activator of Flowering, PNAS (2005) vol. 102, No. 21, p. 7748-7753.
Franziska Turck, et al., Regulation and Identity of Florigen: Flowering Locus T Moves Center Stage, Annual Review of Plant Biology (2008) vol. 59, p. 573-594.
Ballerini and Kramer: In light of evolution: a re-evaluation of conservation in the CO-FT regulon and its role in photoperiodic regulation of flowering time, Frontiers in Plants Science, 2, 1-13, 2011.
Schwartz, et al.: Cis—regulatory changes of flowering locus T mediate nature variation and flowering responses of *Arabidopsis thaliana*, Genetics 183, 723-732, 2009.

* cited by examiner

*Primary Examiner* — Anne Kubelik
*Assistant Examiner* — Charles Logsdon
(74) *Attorney, Agent, or Firm* — Vedder Price P.C.; Thomas J. Kowalski; Deborah L. Lu

(57) ABSTRACT

A plant comprising a modified Flowering Locus (FT) polynucleotide expressing a modified polypeptide exhibits altered flowering time, floral numbers and/or increased seed production. Different mutant sequences conferring different phenotypes are disclosed.

15 Claims, 15 Drawing Sheets

Figure 2A-B a

Construction of single amino acid (AA) FT mutants

| Single AA FT mutant | Primers | | | |
|---|---|---|---|---|
| | A | B | C | D |
| PVX/FT$_{L67A}$ | PP331 | PP527 | PP528 | PP332 |
| PVX/FT$_{V68A}$ | PP331 | PP529 | PP530 | PP332 |
| PVX/FT$_{V70A}$ | PP331 | PP531 | PP532 | PP332 |
| PVX/FT$_{D71A}$ | PP331 | PP533 | PP534 | PP332 |
| PVX/FT$_{P72A}$ | PP331 | PP535 | PP536 | PP332 |
| PVX/FT$_{D73A}$ | PP331 | PP537 | PP538 | PP332 |
| PVX/FT$_{P77A}$ | PP331 | PP539 | PP540 | PP332 |
| PVX/FT$_{S78A}$ | PP331 | PP541 | PP542 | PP332 |
| PVX/FT$_{Y85A}$ | PP331 | PP543 | PP544 | PP332 |
| PVX/FT$_{R119A}$ | PP331 | PP545 | PP546 | PP332 |
| PVX/FT$_{Q140A}$ | PP331 | PP547 | PP548 | PP332 |
| PVX/FT$_{G172A}$ | PP331 | | | PP549 |
| PVX/FT$_{R173A}$ | PP331 | | | PP551 |
| PVX/FT$_{R174A}$ | PP331 | | | PP552 | b

PVX/FTmutant

PVX/FT

PVX/mFT

PVX

Figure 3A-I
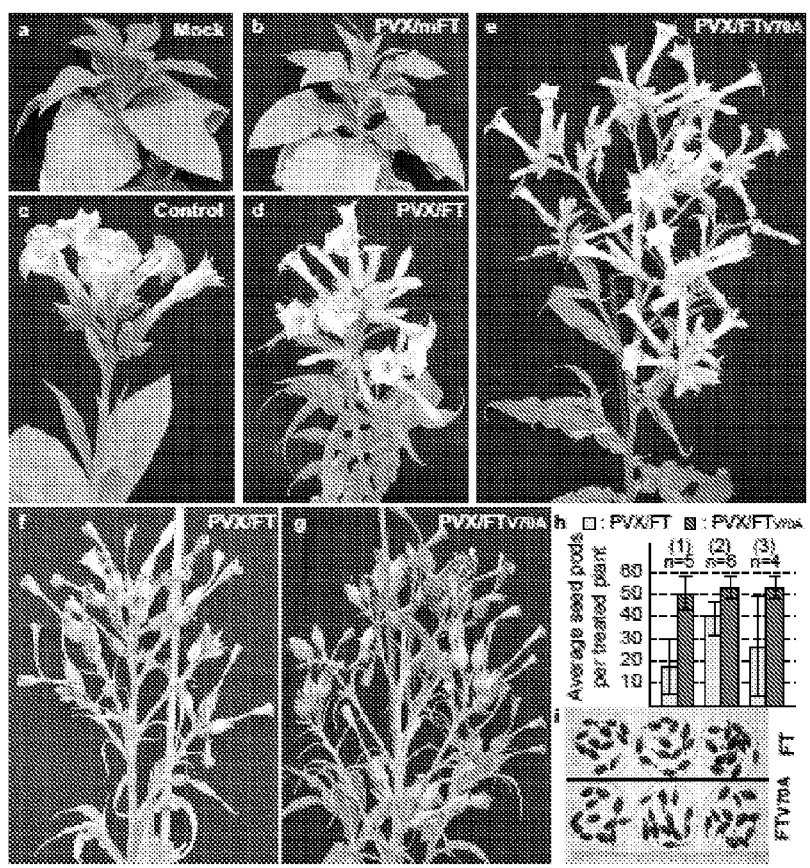

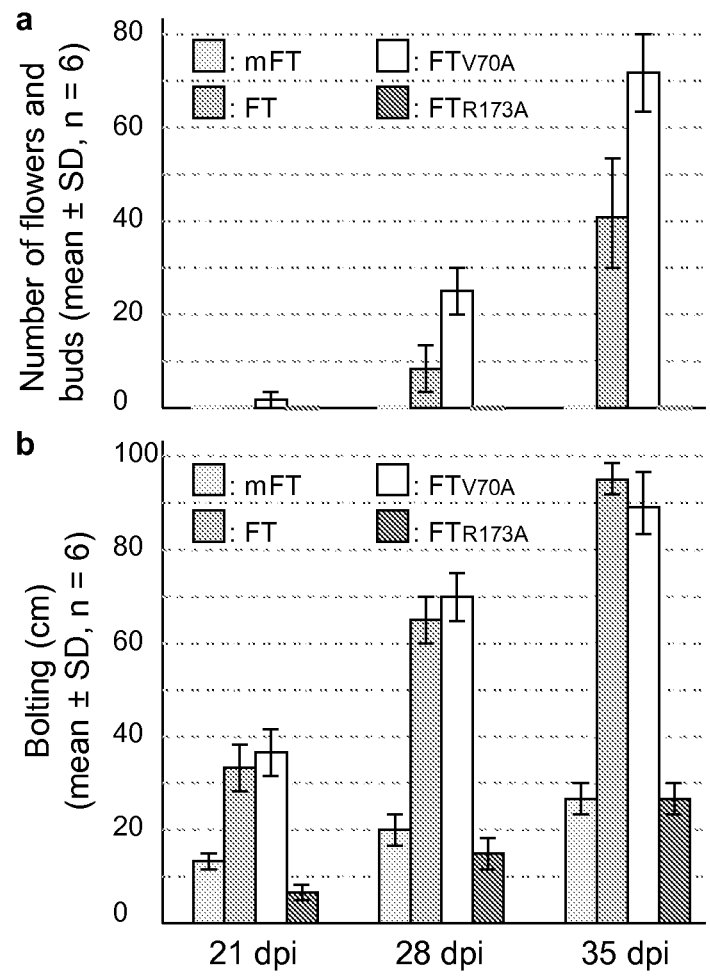
Figure 4A-B

Figure 6
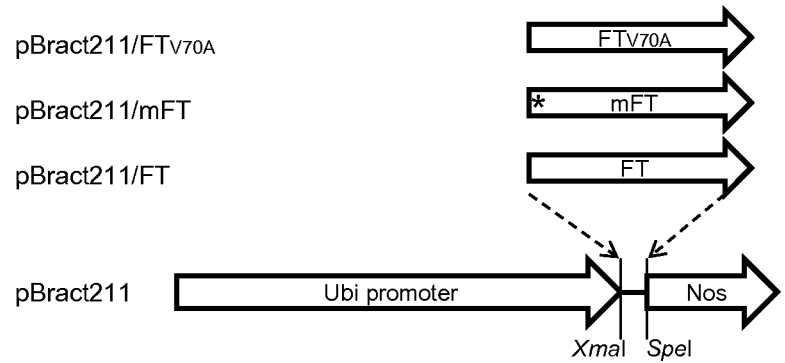
Figure 7A-C
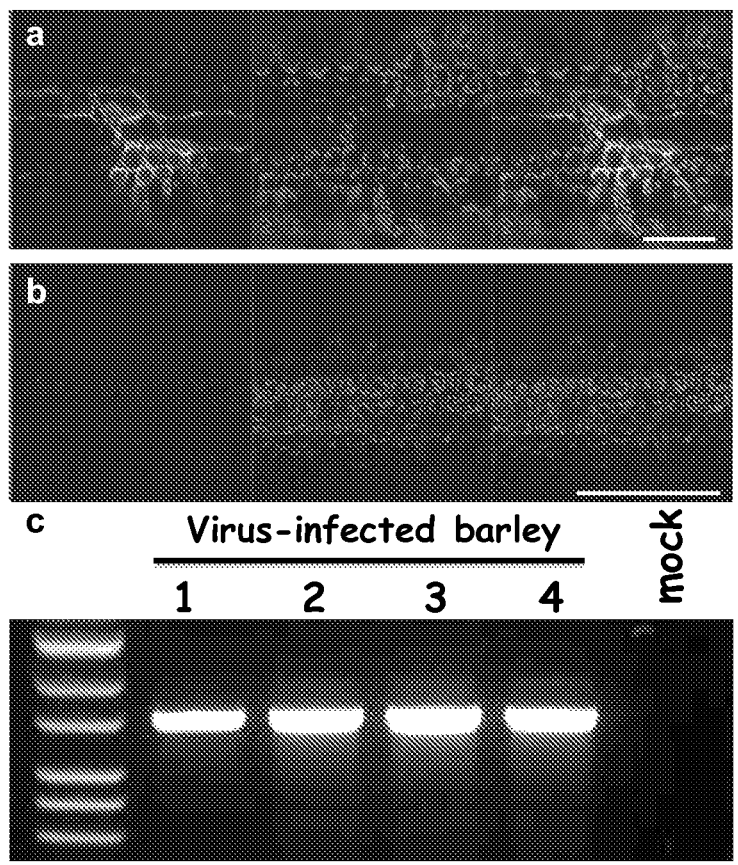

Figure 8A-D
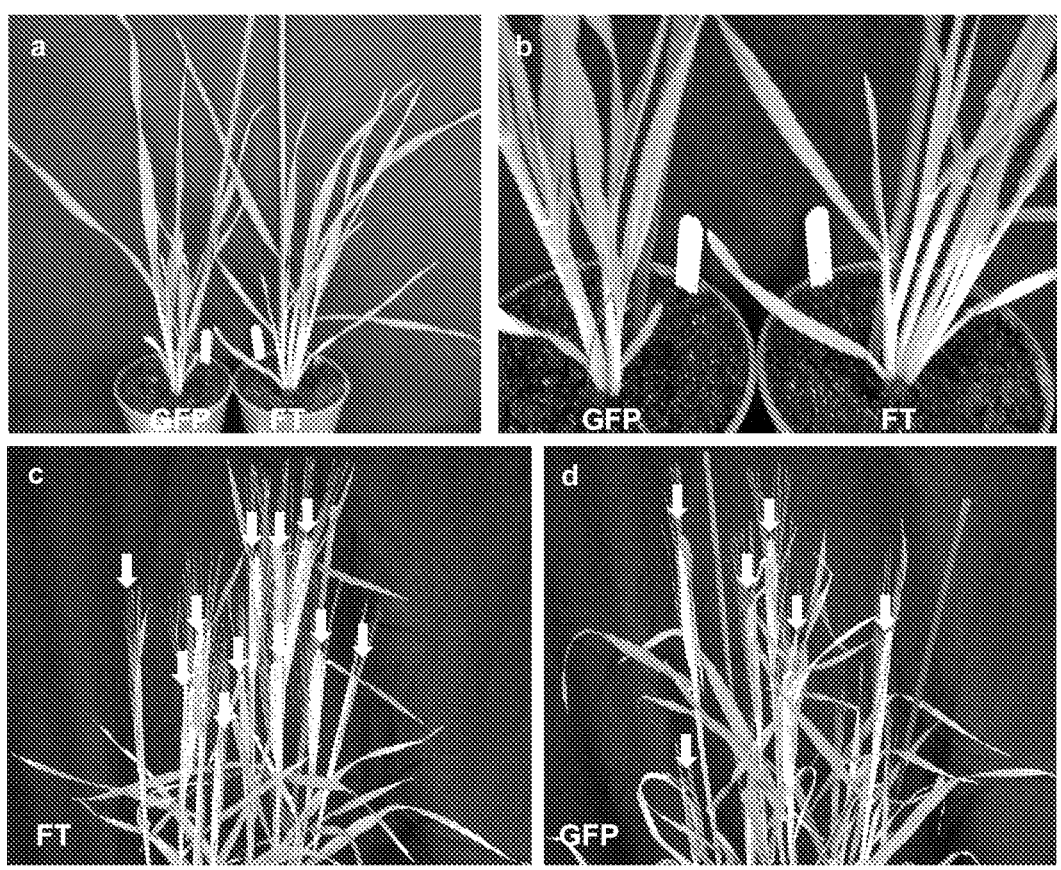

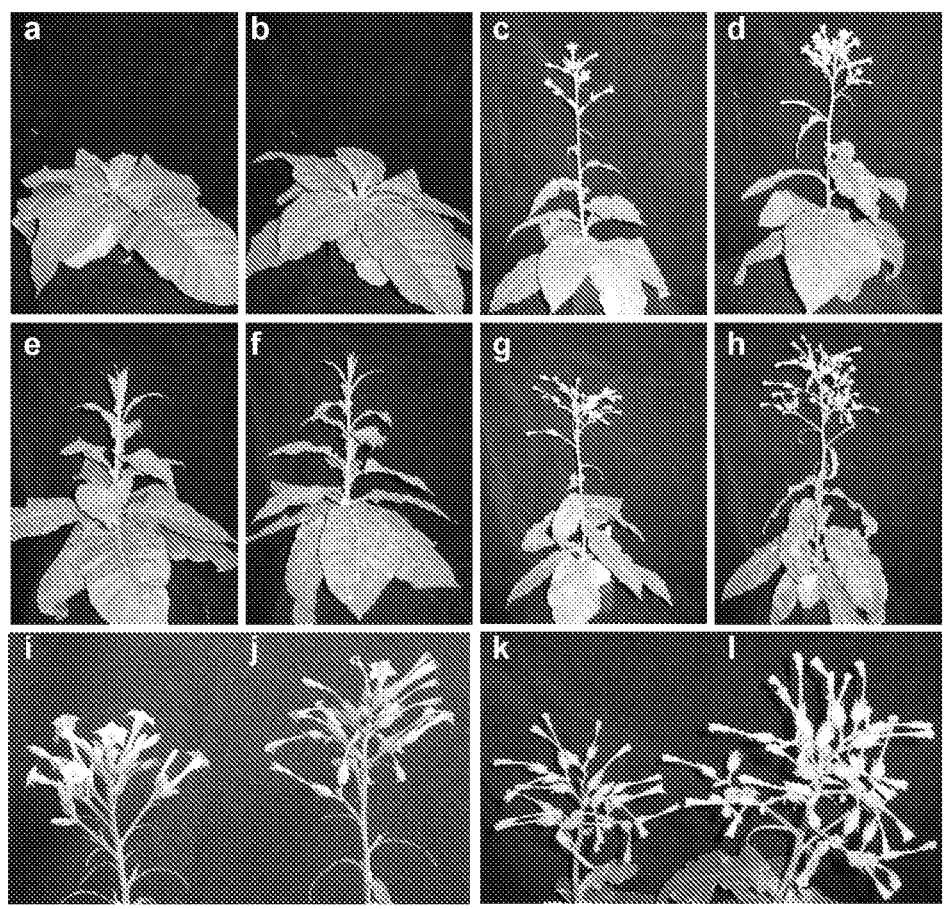
Figure 9A-L

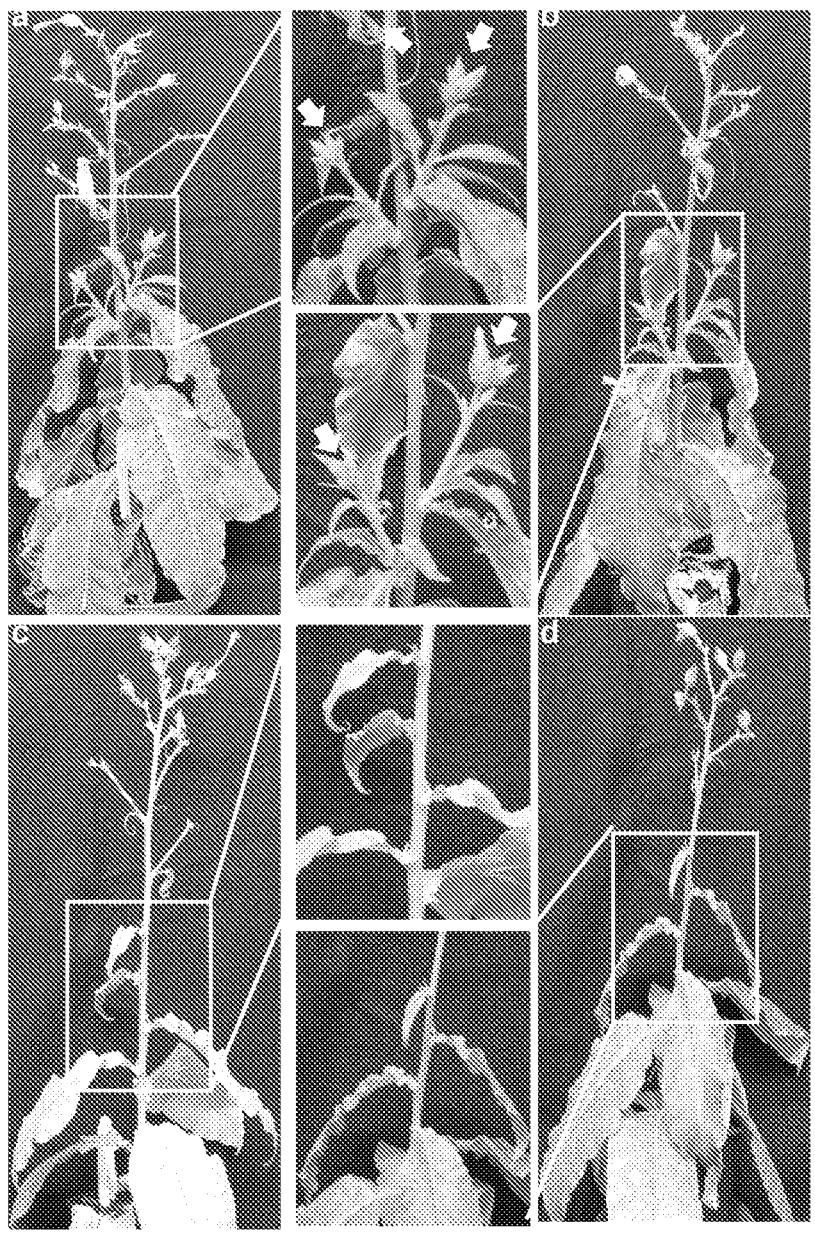
Figure 10A-D

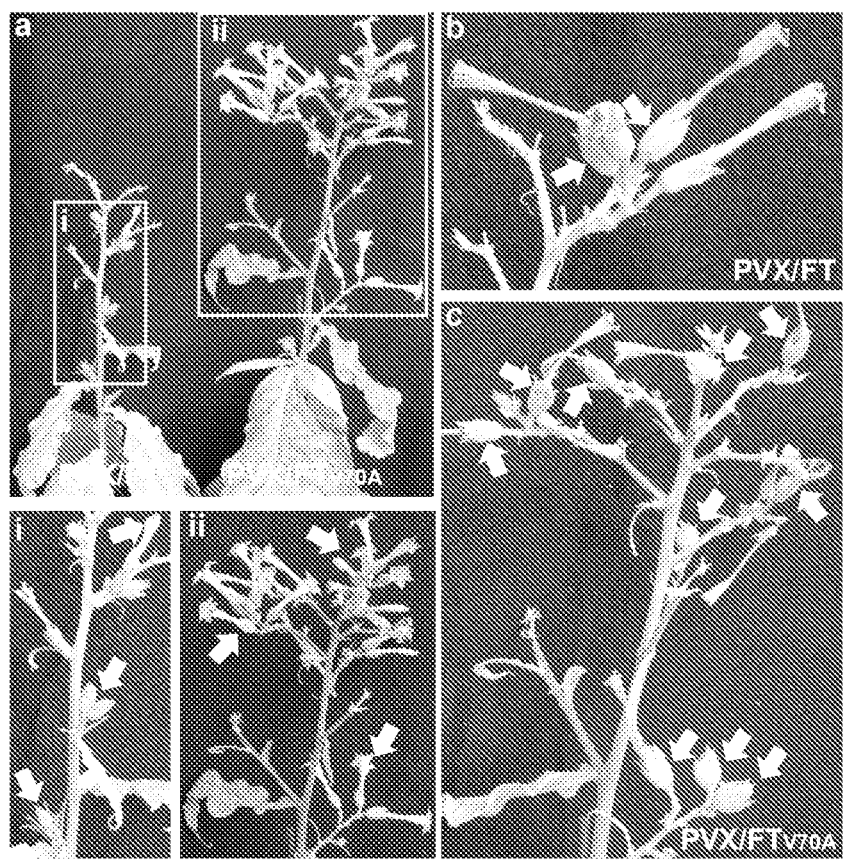
Figure 11A-C

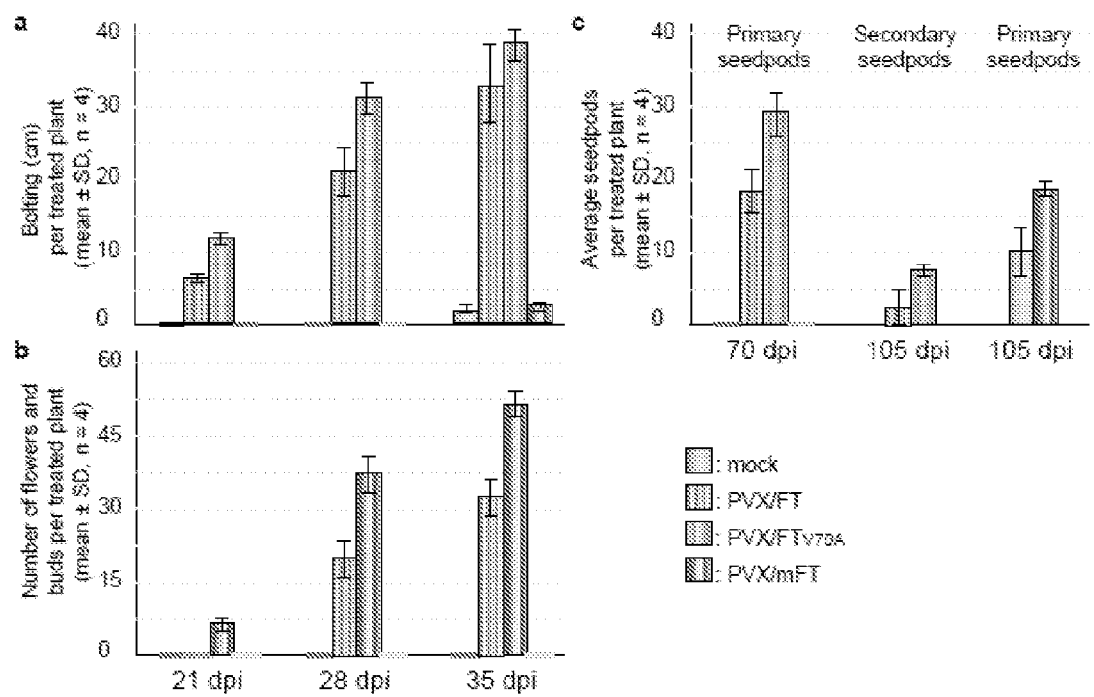
Figure 12A-C mFT wtFT

FTv70 mFT wtFT

FTv70

MOLECULAR ENGINEERING OF A FLORAL INDUCER FOR CROP IMPROVEMENT

RELATED APPLICATIONS AND INCORPORATION BY REFERENCE

This application is a continuation-in-part application of international patent application Serial No. PCT/GB2011/050440 filed 7 Mar. 2011, which published as PCT Publication No. WO 2011/107808 on 9 Sep. 2011, which claims benefit of GB patent application Serial No. 1003702.6 filed 5 Mar. 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted in ASCII format via EFS-Web and is hereby incorporated by reference in its entirety. Said ASCII copy, created on Jul. 15, 2013, is named 44445.00.2001_SL.txt and is 99,898 bytes in size.

FIELD OF THE INVENTION

The invention relates to plants with altered flowering time, floral numbers and/or seed production and provides methods for producing such plants.

BACKGROUND OF THE INVENTION

Flowering time in photoperiodic flowering plants is a key developmental switch that is affected by environmental signals perceived by the leaves. An important component of the signalling pathway that regulates flowering is the Flowering Locus T (FT) gene. When a plant is induced to flower a phloem-mobile signal termed "florigen" is produced which is transported through the phloem translocation stream to the shoot apical meristem (SAM) where it induces floral development[1,2]. In Arabidopsis, the mobile florigen has been shown to be encoded by the Flowering Locus T (FT) gene. FT transcribes mRNA specifically in phloem cells but not in the SAM[3]. Its protein product, however, functions at the shoot apex[4-6]. Arabidopsis FT is a small globular 23 kd protein consisting of 175-amino acids (aa) with homology to the mammalian phosphatidylethanolamine binding protein (PEBP) or Raf kinase inhibitor protein. FT belongs to a group of six closely related proteins, which includes TFL1 and CENTRORADIALIS (CEN) of Antirrhinum.

There is collective evidence that the Arabidopsis FT protein[7,8] and its tomato SFT[9], rice Hd3a[10] and Cucurbit Cm-FTL½[11] orthologs act as a component of the non cell-autonomous flowering signal that is transported through the phloem into the SAM, whilst the role of FT mRNA movement in long-distance florigenic signalling remains unknown[12]. Once FT is present in the SAM, it interacts with a bZIP transcription factor, FD, encoded by Flowering Locus D to activate floral identity genes such as APETELA 1 and SUPPRESSOR OF OVEREXPRESSION OF CO1. The latter activates LEAFY and induces flowering[4,6]. Natural genetic variation in genes controlling the expression of the rice FT ortholog Hd3a, and in Hd3a itself, contribute to diversity of flowering time in cultivated rice[13]. Overexpression of FT in transgenic plants from several species is associated with early flowering. U.S. Pat. No. 6,225,530 describes an isolated polynucleotide encoding an FT polypeptide. Hanzawa et al also describes modified FT and their expression sequence in plants[14].

Flowering time and quantity of flowers (and seed) are crucial aspects of crop yield and quality and there is a need in agriculture to create new tools to control the time and amount of flowering and seed production in a wide variety of plant species. As well as enhancing plant productivity by increasing flowering, in certain plant species it is desirable to delay or prevent flowering altogether. The present invention is aimed at addressing these needs. Bioengineering of FT or creating novel FT alleles by TILLING, mutation breeding and selection of FT may provide useful alleles for breeding of novel crops to enhance productivity to meet rapid increase of global demand for food, feed and fuel.

Citation or identification of any document in this application is not an admission that such document is available as prior art to the present invention.

SUMMARY OF THE INVENTION

The Flowering Locus T (FT) is a key component of the floral signalling pathway. FT is known to be involved in controlling flowering time. Surprisingly, the inventors have found that altering the amino acid sequence of the FT protein may also increase the number of flowers and seed yield. Applicants disclose that modification of FT leading to single amino acid changes provides novel gene alleles with the surprising potential for molecular breeding to increase crop productivity. Using an alanine scanning approach and a plant virus-based floral induction system, Applicants describe the molecular engineering of the Arabidopsis FT protein to produce a modified FT with an altered phenotype, for example enhanced ability to trigger flowering, resulting in more flowers and an increase in seed yield. Modification of conserved residues within the FT sequence results in an altered phenotype when the modified gene is expressed in plants.

Thus, the invention relates to transgenic plants expressing a modified FT gene or polynucleotide said gene encoding a modified amino acid (aa) sequence characterised in that said expression results in a phenotype that is different from the wild type phenotype and different from plants overexpressing wild type FT. The gene is modified in such a way that a conservative residue in the FT aa sequence is altered. Other aspects of the invention relate to methods for producing such plants.

In one aspect, the invention relates to a transgenic plant which may comprise and expressing a modified FT polynucleotide said polynucleotide encoding a modified polypeptide which may comprise an amino acid modification wherein said plant exhibits an altered flowering profile.

Specifically, the invention relates to a transgenic plant which may comprise and expressing a modified FT polynucleotide said polynucleotide encoding a modified polypeptide which may comprise an amino acid modification wherein said plant exhibits one of the following phenotypes:
(a) increased flowering;
(b) increased flowering and increased fruit and/or seed production;
(c) no bolting and no flowering;
(d) normal bolting and delayed flowering provided that the amino acid modification does not comprise Y85H or
(e) normal bolting and no flowering.

In one aspect, the invention relates to a transgenic plant which may comprise and expressing a modified FT polynucleotide said polynucleotide encoding a modified polypeptide which may comprise an amino acid modification wherein said plant exhibits increased flowering and increased fruit and/or seed production.

In another aspect, the invention relates to a method for producing a plant as defined above which may comprise introducing and expressing a modified FT polynucleotide in said plant wherein the polynucleotide encodes a modified polypeptide which may comprise an amino acid modification.

In further aspect, the invention relates to a method for inducing increased flowering and increased seed production in a plant which may comprise introducing and expressing a modified FT polynucleotide in said plant wherein the polynucleotide encodes a modified polypeptide which may comprise an amino acid modification.

In further aspect, the invention relates to an isolated nucleic acid molecule or sequence said nucleic acid encoding a modified polypeptide which may comprise an amino acid modification wherein said modification results in an altered phenotype when said nucleic acid is introduced in a plant wherein said phenotypes is selected from:
(a) increased flowering;
(b) increased flowering and increased fruit and/or seed production;
(c) no bolting and no flowering;
(d) normal bolting and delayed flowering provided that the amino acid modification does not comprise Y85H or
(e) normal bolting and no flowering.

In another aspect, the invention relates to an isolated nucleic molecule or sequence acid said nucleic acid encoding a modified polypeptide which may comprise an amino acid modification wherein said modification consists of or may comprise a substitution of one or more of the following residues: V70, D73, R119, R173, D71, L67, S78 or Q140.

In another aspect, the invention relates to the use of an isolated nucleic acid encoding a modified polypeptide which may comprise an amino acid modification to alter the amount of flowers and/or seed and/or fruit yield in a plant.

The invention also relates to a modified plant which may comprise an isolated nucleic molecule or sequence acid said nucleic acid encoding a modified polypeptide which may comprise an amino acid modification wherein said modification consists of or may comprise a substitution of one or more of the residues identified in table I, in particular in groups II-V.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 2A-B Construction of 14 virus-based floral induction vectors. (a) PVX vectors and list of primers used in their constructions. (b) Overlapping PCR to produce two overlapping products using primer set A and B, or C and D for construction of PVX/FTmutant. PVX/FT and PVX/mFT were constructed previously[2]. Outline of the PVX-based vector is indicated.

FIG. 3A-I $FT_{V70A}$ has enhanced biological activity in floral induction and seed production. (a-e) Different flowering phenotypes were observed in the SD N. tabacum Maryland Mammoth (MM) plants mock-inoculated (a), or inoculated with PVX/mFT (b), PVX/FT (d) or PVX/$FT_{V70A}$ (e) in the non-inductive LD, and MM plant in inducing SD condition (c). (f, g) Seedpods on SD N. tabacum Maryland Mammoth plants inoculated with PVX/FT (f) or PVX/$FT_{V70A}$ (g). (h) Analysis of average numbers of seedpods per inoculated plants in three separate experiments. Numbers of plants (n) used in each experiment are indicated. Student t-tests of all samples show significant differences (P=0.0002) in the numbers of seedpods per plants inoculated with PVX/$FT_{V70A}$ when compared with PVX/FT. (i) Sizes of seedpods. All plants (a, b, d-g) except the control (c) were growing in LD conditions. Photographs were taken at 7 weeks post inoculation (wpi) (a-e), 12-wpi (f, g) or 14-wpi (i).

FIG. 4A-B $FT_{V70A}$ enhances floral induction. $FT_{V70A}$ causes early floral bud formation and more flowers to be produced (a) although FT and $FT_{V70A}$ have a similar capacity to trigger plants to bolt (b). Six SD N. tabacum Maryland Mammoth plants were inoculated with PVX/mFT (mFT), PVX/FT (FT), PVX/$FT_{V70A}$ ($FT_{V70A}$), or PVX/$FT_{R173A}$ ($FT_{R173A}$). Bolting was measured by the stem height and numbers of flowers and floral buds were counted at 21, 28 and 35 days post-inoculation (dpi). $FT_{R173A}$, the loss-of-function mutant of FT (Table 1), was used as an additional control.

FIG. 5(c) discloses SEQ ID NOS 89, 94, 99, 88, 93, 98, 90, 95, 100, 91, 96, 101, 92, 97 and 102, respectively, in order of appearance. The sizes and positions of the 1-kb DNA ladder and the RT-PCR products are indicated. Nucleotide mutations for changing the amino acids of the FT protein are underlined. (d-e) Western blot analysis of FT protein (d) and the PVX coat protein (e) in SD *N. tabacum* Maryland Mammoth plants. (f) Coomassie blue-stained gel showing equal loading of soluble proteins extracted from young leaves of plants mock-inoculated, or inoculated with PVX/mFT, PVX/FT, PVX/FTV70A or PVX/FTR173A at 5-wpi. The positions and sizes of the protein markers, FT and PVX CP are indicated. FTR173A a newly identified loss-of-function mutant of FT (Table 1), was used as an additional control.

FIG. 6 Construction of FT over expression cassette for barley transformation. Coding sequences for the *Arabidopsis* FT and its novel alleles are to be amplified by PCR using high fidelity pfu polymerase, specific primers and cDNA clones (FIG. 1a) as templates, digested with XhoI and SpeI, and cloned into the XhoI/SpeI sites of the binary vector pBract211 to produce pBract211/FT (control), pBract211/mFT (control) and pBract211/FT$_{V70A}$. The three expression cassettes are to be used for barley transformation.

FIG. 7A-C GFP expression via a virus-based vector in barley. The infectious cDNA clone of the cocksfoot mild mosaic virus (CMMV)[17] was modified to produce a vector for in vitro production of a new species of subgenomic (sg) RNA. This new sgRNA encodes the mRNA of the gene of interest to replace the viral coat protein gene and acts as mRNA for protein translation. The GFP coding sequence was cloned in the newly constructed CMMV vector. Barley leaf tissues mixed inoculated with CMMVgenomic RNA and the new sgRNA-GFP transcripts showed GFP green fluorescence (a; left: GFP fluorescence, middle: chlorophyll auto-fluorescence; right: merged image), revealed by Confocal microscopic examination. However, no GFP specific fluorescence was observed in mock-inoculated barley plants (b). Viral expression of GFP mRNA in infected plants was readily detectible by RT-PCR (c). Bar=100 µm.

FIG. 8A-D Improved production of tillers and heads with kernels by FT in barley. The wild type *Arabidopsis* FT coding sequence was cloned in the newly constructed CMMV vector. Young barley plants were mixed inoculated with CMMVgenomic RNA and the sgRNA-FT or the sgRNA-GFP transcripts. The latter was used as a negative control. Viral expression of FT caused early plant development and increased number of tillers after 16 days post inoculation, compared with plants having GFP expression (a, b). After 65 days post-inoculation, FT-expressing barley plants (c) developed more heads with kernels (indicated by arrows) than GFP-expressing plants (d).

FIG. 9A-L FT$_{V70A}$ possesses an enhanced biological activity in floral induction and seed production in *N. tabacum* Maryland Mammoth (MM) in SD. MM plants were mock inoculated (a, e, i) or treated with PVX/mFT (b, f, j), PVX/FT (c, g, k) or PVX/FT$_{V70A}$ (d, h, l) and grown in a 12-hr SD photoperiod of light at 25° C. Photographs were taken at 35—(a-d), 56—(e-h, k, l) and 84—(i, j) days post inoculation. Mock-inoculated (i) or PVX/mFT (j)-treated plants eventually flowered and produced seedpods.

FIG. 10A-D Viral transient expression of FT$_{V70A}$ promote secondary budding and flowering in *N. tabacum* Maryland Mammoth (MM) in SD. MM plants were treated with PVX/FTV70A (a,b) or PVX/FT (c,d), and grown in a 12-hr photoperiod of light at 25° C. FTV70A (a, b) possesses an enhanced function in comparison to FT (c,d) in triggering development of lateral shoots from which axillary floral buds and flowers continued to develop. Mature seedpods produced from primary flowers were harvested at 70 days post inoculation (dpi). Remaining non-mature primary seedpods attach to plants treated with PVX/FT (c,d). Photographs were taken at 70 dpi. The outlined portions of plants are enlarged to show axillary shoots and newly developed floral buds (arrow).

FIG. 11A-C Viral transient expression of FT$_{V70A}$ promote secondary budding and flowering in *N. tabacum* Maryland Mammoth (MM) in SD. MM plants were treated with PVX/FT or PVX/FT$_{V70A}$, and grown in a 12-hr photoperiod of light at 25° C. Expression of FT$_{V70A}$ induced further development of axillary shoots, secondary floral buds, flowers and seedpods (arrow, a-c). Mature seedpods produced from primary flowers were harvested at 70 days post of inoculation (dpi) of plants. Photographs were taken at 84 (a) or 98 dpi (b, c). The boxed sections of plants (i, ii) are enlarged to show axillary shoots and newly developed secondary floral buds and flowers.

FIG. 12A-C FT$_{V70A}$ enhances floral induction and seed production in *N. tabacum* Maryland Mammoth (MM) in SD. Expression of FT or FTV70A from PVX/FT or PVX/FT$_{V70A}$ is effective to induce early bolting and flowering when compared to mock- or PVX/mFT-treatment (a, b). However, MM plants treated from PVX/FT$_{V70A}$ produced significantly more numbers of flowers and seedpods than these treated with PVX/FT (b, c). Bolting was measured by stem height and numbers of flowers and floral buds were counted at 21, 28 and 35 days post inoculation (dpi). Total primary and secondary seedpods were counted at 70 dpi and 105 dpi.

FIG. 13(b) discloses SEQ ID NO: 103, FIG. 13(c) discloses SEQ ID NO: 104 and FIG. 13(d) discloses SEQ ID NO: 105. (f-g) Western blot analysis of the *Arabidopsis* FT protein and PVX CP. No endogenous or viral transient FT protein was detected in the mock-inoculated MM plant or in plant treated with PVX/mFT. However, expression of the *Arabidopsis* FT protein was readily detectable in MM plants treated with either PVX/FT or PVX/FTV70A (f). The viral CP was detected in plants treated with PVX/mFT, PVX/FT or PVX/FTV70A, but not in the mock-inoculated plant (g). Coomassie blue-stained gel indicates the equal loading of total soluable protein samples (h). The positions and sizes of 1.0-kb DNA and the protein markers (M) are indicated.

FIG. 15A-F 2M Transgenic Barley Transformation of barley. The Spring barley, Golden Promise, transformed with pBract214-FT$_{V70A}$, produce more heads than barley transformed with either pBract214-FT or pBract214-mFT. Photographs were taken at 2 months post-transformation.

FIG. 16 4M Transgenic Barley. Transgenic expression of FTV70A significantly increases barley yields. Grains were counted from heads of individual barley plants transformed with pBract211-mFT, pBract211-wtFT or pBract211-FTV70A. Comparing FTV70A-expressing to mFT-expressing barley transformants, the total number of grains per line/plant increased approx. 85.7%. Regenerated plants with zero copy of any of three transgene constructs were used as "Null transformation control". Student's t-tests show there is a significant difference in grain production between FTV70A- and mFT-transgenic lines (p=0.017) as well as between FTV70A- and wtFT-transgenic lines (p=0.003) whilst there is no significant difference between mFT- and wtFT-transgenic lines (p=0.178).

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature.

In a first aspect, the invention relates to a transgenic plant which may comprise and expressing a modified FT polynucleotide said polynucleotide encoding a modified polypeptide which may comprise an amino acid modification wherein said plant exhibits one of the following phenotypes:
 (a) increased flowering;
 (b) increased flowering and increased fruit and/or seed production;
 (c) no bolting and no flowering;
 (d) normal bolting and delayed flowering provided that the amino acid modification does not comprise Y85H or
 (e) normal bolting and no flowering.

Figure 1:
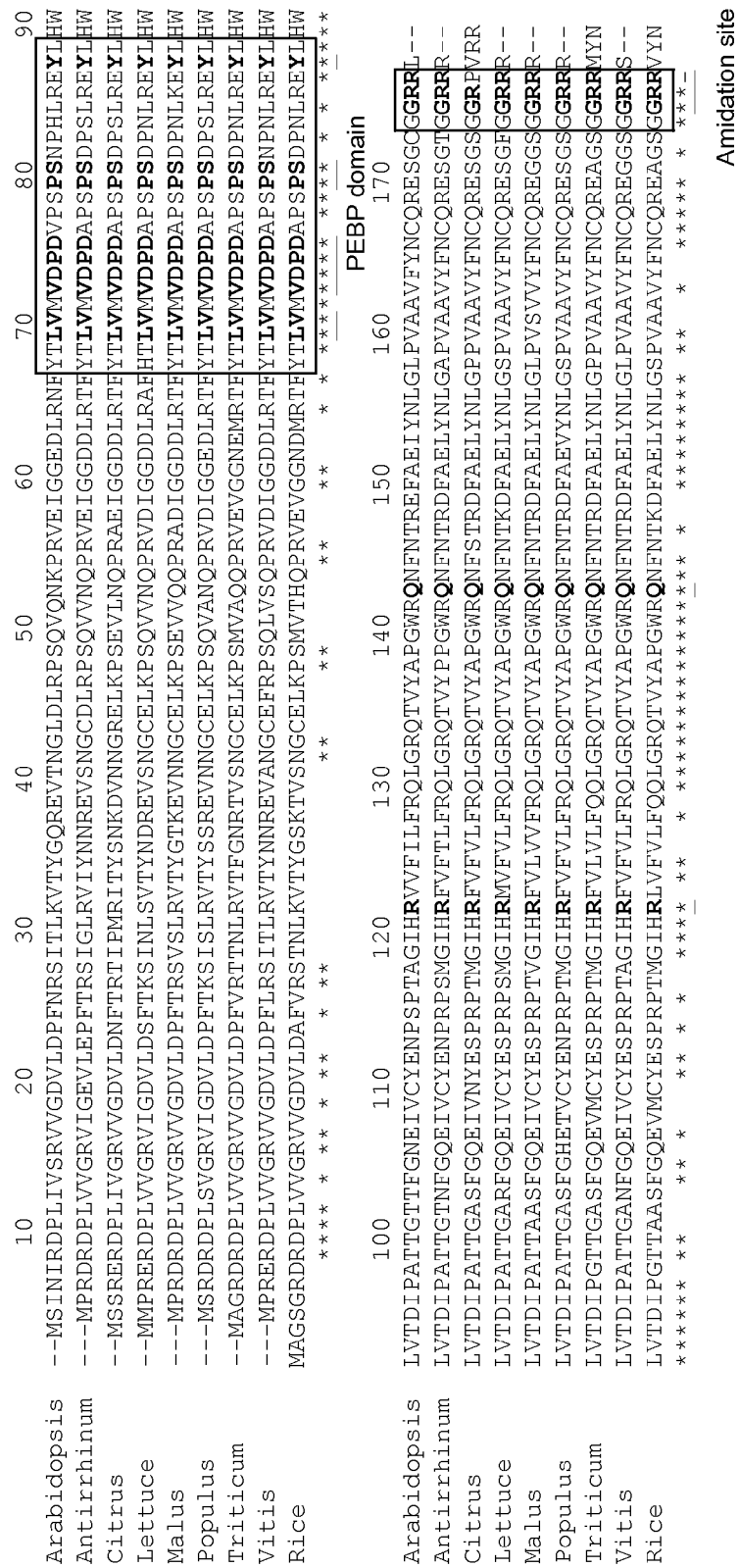
FIG. 1 Comparison of FT amino acid sequences among Arabidopsis (SEQ ID NO: 2) and other plant species (SEQ ID NOS 80-87, respectively, in order of appearance). The phosphatidylethanolamine binding protein (PEBP) domain and the putative amidation site are indicated. The individual amino acid residues selected for modification are in bold. The conserved amino acids (asterisked) among all species are indicated. With respect to FIG. 1, the numbering is based on the numbering of the Arabidopsis sequence. Where reference is made to the Arabidopsis ortholog, two amino acids must be subtracted from the numbering shown in FIG. 1, as the Arabidopsis sequence contains two less amino-terminal amino acids than, for example, the rice ortholog.

*Arabidopsis* FT is a small globular protein consisting of 175-aa with homology to the mammalian phosphatidylethanolamine binding protein (PEBP) or Raf kinase inhibitor protein. The Flowering Locus T (FT) gene is highly conserved amongst different plant species. A comparison of FT amino acid sequences is shown in FIG. 1. Particularly conserved are the PEBP domain and the amidation site. Through comparing the amino acid sequences of *Arabidopsis* FT and its orthologs from rice and other species, Applicants identified 43 aa, including 9 aa within the conserved PEBP domain, 3 aa within a putative amidation site, the arginine residue at position 119 (R119), the glutamine residue at the position of 140 (Q140) and a number of N-terminal residues, as targets for molecular modification.

In the experiments described herein, each amino acid was substituted with Alanine (Ala, A) to produce 43 different single amino acid-modified FT proteins (table 1). This was achieved by PCR and overlapping PCR-based mutagenesis using specific primers (Table 3, example 8). The sequence was then cloned into the potato virus X (PVX)-based floral induction system[12] (FIG. 2b). Using the wild-type FT and a non-sense mutant mFT as positive and negative controls[12] respectively, Applicants found that viral ectopic expression of the fourteen FT derivatives (table 1), confirmed by semi-quantitative (sq)RT-PCR and western blot, produced five different phenotypes in the short-day (SD) *Nicotiana tabacum* Maryland Mammoth (MM) plants in the non-inductive long-day (LD) conditions (Table 1).

TABLE 1

Effect of single amino acid mutation on biological functions of the *Arabidopsis* FT protein

| Group | FT mutants | Phenotypes* |
|---|---|---|
| I | $FT_{V68A}$, $FT_{P72A}$, $FT_{P77A}$, $FT_{G172A}$, $FT_{R174A}$, $FT_{S2A}$, $FT_{I5A}$, $FT_{R6A}$, $FT_{P8A}$, $FT_{V11A}$, $FT_{S12A}$, $FT_{R13A}$, $FT_{D20A}$, $FT_{P21A}$, $FT_{N23A}$, $FT_{R24A}$, $FT_{S25A}$, $FT_{I26A}$, $FT_{L28A}$, $FT_{T31A}$ | Normal bolting and flowering |
| II | $FT_{L67A}$, $FT_{S78A}$, $FT_{Q140A}$, $FT_{G16A}$, $FT_{L19A}$, $FT_{F22A}$, $FT_{K29A}$, $FT_{V30A}$ | Normal bolting but delayed flowering |
| III | $FT_{D71A}$, $FT_{Y85A}$, $FT_{I3A}$, $FT_{N4A}$, $FT_{D7A}$, $FT_{L9A}$, $FT_{V14A}$, $FT_{V15A}$, $FT_{D17A}$, $FT_{V18A}$ | Normal bolting but no flowering |
| IV | $FT_{D73A}$, $FT_{R119A}$, $FT_{R173A}$ | No bolting, no flowering |
| V | $FT_{V70A}$, $FT_{T27A}$ | Slightly early flowering but increasing floral numbers and seed production per treated plant |

*Phenotypes are compared to that of MM plants treated with PVX expressing the *Arabidopsis* wtFT protein These data demonstrate that the different conserved amino acids identified herein have different influences on FT biological activity and without wishing to be bound by theory, it is likely that they may do this by affecting different aspects of FT protein function, e.g. non-cell-autonomous florigen signalling and/or cell-autonomous floral induction. The different aspects of the invention described herein make use of the specific amino acid changes in the FT polypeptide as detailed in table 1. Specifically, transgenic plants expressing a modified FT nucleotide encoding a FT peptide with an altered sequence as compared to the wild type sequence as described in any of the mutant groups I to V as defined above (or equivalent mutations in orthologous sequences) are within the scope of the invention.

A modified FT polynucleotide according to the invention is a modified nucleic acid sequence, i.e. a modified FT gene that differs from the wild type polynucleotide, gene or nucleic acid sequence in its sequence.

Wild type as used herein refers to a plant that has not been modified and is preferably of the same species. The increase described herein may be two-fold or more, or describe an increase of at least 10-50%, for example at least 10%, at least 20%, at least 30%, at least 40%, at least 50% or more.

Generally, for the purposes of the invention, "transgenic", "transgene" or "recombinant" means with regard to, for example, a nucleic acid sequence, an expression cassette, gene construct or a vector which may comprise the nucleic acid sequence or an organism transformed with the nucleic acid sequences and expressing the nucleic acid sequences, expression cassettes or vectors according to the invention, all those constructions brought about by recombinant methods in which either
 (a) the nucleic acid sequences encoding proteins useful in the methods of the invention, or (b) genetic control sequence(s) which is operably linked with the nucleic acid sequence according to the invention, for example a promoter, or (c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined herein—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the different embodiments of the invention are at their natural position in the genome of a plant, the sequence has been modified with regard to the natural sequence, and/or that the regulatory sequences of the natural sequences have been modified. Specifically, transgenic plants may refer to plants generated by methods that do not solely relay on traditional breeding. The plants may not carry a "transgene", but may be generated through mutagenesis. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein. The modified FT polynucleotide encodes a modified polypeptide that differs from the wild type polypeptide in its amino acid sequence. The modified polypeptide may comprise an amino acid modification, for example a deletion, addition or substitution. Preferably, the modification is an amino acid substitution of one or more amino acids within the sequence. In one preferred embodiment, the modification consists of a single amino acid substitution. The substitution may be conservative or non-conservative. In one embodiment, the substitution is a non conservative substitution, i.e. the amino acid is replaced with another amino acid that does not share the same chemical properties. Most preferred are substitutions with a neutral amino acid that cause little change in protein structure, for example Alanine (Ala, A) or Phenylalanine (Phe, F).

A preferred substitution is one that causes little change in protein structure. For example, mutation to A allows protein folding while at the same time affecting the biological function of the peptide. Where the chemical properties of the particular amino acid that is altered are critical to wild-type function, alteration of said amino acid produces a different phenotype in the mutant plant. However, based on the information provided herein, those skilled in the art will appreciate that amino acid substitutions other than those with A disclosed herein are also within the scope of the invention and that replacements with other amino acids, in particular those that allow protein folding but have different properties from the native residue are expected to have similar effects. Such replacements are therefore within the skill of the skilled person.

A skilled person will appreciate that to achieve the desired amino acid substitutions, the corresponding codon must be altered and due to the degenerate code of the DNA, more than one alteration of the target codon may be possible to generate the desired substitution in the peptide.

The plant according to the invention exhibits a phenotype that is different from the wild type phenotype. In particular, the plant exhibits an altered flowering profile. The term flowering profile may relate to an increase in flowering and/or a change in flowering time. Increased flowering as used herein is understood to mean increased numbers of flowers per plant, thus leading to an increase in seed yield. Flowering time may be early or delayed. For example, plants that flower early start to flower one week earlier than plants expressing the wild-type FT. Plants that exhibit delayed flowering, start to flower one week later than plants expressing the wild-type FT. However, the inventors have surprisingly found that altering the amino acid sequence of the FT protein may also increase the number of flowers and seedpods. An increase in seed yield was also observed (Table 1, FIG. 3).

Thus, in a preferred embodiment, the invention relates to a transgenic plant which may comprise and expressing a modified FT polynucleotide said polynucleotide encoding a modified polypeptide which may comprise an amino acid modification wherein said plant exhibits increased flowering and increased yield, i.e. increased fruit and/or seed production. The disclosure provides examples of such modifications. For example, the modification is a substitution and said substitution may comprise or consists of substitution of V70 or T27 or both. The substitution may be with A. Thus, in the modified FT polynucleotide, the codon encoding V70 and/or T27 may be changed to a codon encoding A (GCU, GCC, GCA, GCG). The plant may further show altered flowering time.

The numbering of the amino acid residues as used in this disclosure is based on the numbering of the *Arabidopsis* FT amino acid sequence. This numbering is shown in FIG. 1. Thus, V70 in the *Arabidopsis* FT amino acid sequence is the second V residue in the conserved PEBP domain (YTLVMVDPDVPSPSNPHLREYL (SEQ ID NO: 79)). Because the FT amino acid sequence in other species may comprise fewer or more amino acids (most typically, 1 to 2 additional or fewer amino acids), the position of the second conserved V residue in the amino acid sequence may not be 70, but may be 69, 71 or 72. The positions of the targeted residues according to the invention in some exemplified plant species are shown in FIG. 1. In other words, according to one embodiment of this aspect of the invention, the modification is a substitution and said substitution may comprise or consists of substitution of the second conserved V in the PEBP domain which may comprise the following sequence or a sequence at least 90% homologous thereto: YTLVMVDPDVPSPSNPHLREYL (SEQ ID NO: 79). In another embodiment, an N terminal residue at about position 27 is modified.

A peptide sequence expressed by said plant is shown in SEQ ID NO. 44 and 45. Homologous or orthologous sequences from other plants that carry the mutation at an equivalent position are within the scope of the invention.

The correlation between the biological function and the expression of the engineered $FT_{V70A}$ protein was analysed in three separate experiments. SD MM tobacco plants that were mock-inoculated or treated with PVX/mFT carrying a mutated nontranslatable FT mRNA remained vegetative in LD (FIG. 3*a, b*) while positive control plants (FIG. 3*c*) and MM plants treated with PVX/FT that had the capacity to express normal FT protein flowered (FIG. 3*d*). By contrast, viral ectopic expression of $FT_{V70A}$ triggered early floral bud formation and flowering (FIG. 4*a*), and resulted in a marked increase in flower numbers per inoculated plants (FIG. 3*e*), although both FT and $FT_{V70A}$ had a similar capacity to induce MM tobacco to bolt (FIG. 4*b*). $FT_{V70A}$-, but not FT-expressing MM tobacco plants were consistently found to bear significantly high numbers of seedpods (FIG. 3*f-h*). The increased number of seedpods did not result in a reduced size of seedpods (FIG. 3*i*). Consequently, total dry weight seed production was approx. 30% greater in plants treated with PVX/$FT_{V70A}$ compared to plants treated with PVX/FT. Moreover, seeds collected from the PVX/$FT_{5A}$-treated plants were found to have the same germination vigour of the seeds as compared with normal MM tobacco seeds. The plant also shows early flowering at 21 days post inoculation, which is approx. one week earlier than plants inoculated with the recombinant virus expressing wild-type FT (FIG. 4). Moreover, the plant is characterised in an increase in flowers, approx 72 flowers/plant compared to approx. 40 flowers per wild-type FT expressing plant (FIG. 4).

Thus, according to one of the preferred aspects of the invention, the plant shows an increase in seed production or seed yield wherein said increase is about 10% to about 50% or more, for example about 30%. The increase in flowering may be 10% to about 50% or more.

In another embodiment, the invention relates to a plant which may comprise and expressing a modified FT polynucleotide said polynucleotide encoding a modified polypeptide which may comprise an amino acid modification wherein said plant exhibits no bolting and no flowering. In one embodiment, the substitution may comprise or consists of substitution of an amino acid at residues D73, R119 or R173. The substitution may be with A. As mentioned above, the numbering of the targeted conserved amino acid residues as used in this disclosure is based on the numbering of the *Arabidopsis* FT amino acid sequences. The conserved D at position 73 is the first D in the conserved PEBP domain. The conserved R at position 173 is the first R residue in the amidation site. Combinations of the mutations listed above may also be used.

A peptide sequence expressed by said plant is shown in SEQ ID NO. 41 and 43. Homologous or orthologous sequences from other plants that carry the mutation at an equivalent position are within the scope of the invention.

In another embodiment, the invention relates to a plant which may comprise and expressing a modified FT polynucleotide said polynucleotide encoding a modified polypeptide which may comprise an amino acid modification wherein said plant exhibits normal bolting and delayed flowering provided that the amino acid modification does not comprise Y85H. In one embodiment, the substitution may comprise or consists of substitution of an amino acid at residues L67, S78, Q140, G16, L19, F22, K29 or V30. In a preferred embodiment, the substitution may comprise or consists of substitution of an amino acid at residues L67, S78 or Q140. The substitution may be with A. As mentioned above, the numbering of the conserved amino acid residues targeted as used in this disclosure is based on the numbering of the *Arabidopsis* FT amino acid sequences. For example, L67 designates the first conserved L in the PEBP domain, S78 designates the second conserved S in the PEBP domain and Q140 designates the conserved Q in the external loop that is shown to be positioned closed to the Y85 within the ligand-binding sites. Combinations of the mutations listed above may also be used.

A peptide sequence expressed by said plant is shown in SEQ ID NO. 23 and 30. Homologous or orthologous sequences from other plants that carry the mutation at an equivalent position are within the scope of the invention.

In another embodiment, the invention relates to a plant which may comprise and expressing a modified FT polynucleotide said polynucleotide encoding a modified polypeptide which may comprise an amino acid modification wherein said plant exhibits normal bolting but no flowering. In one embodiment, the substitution may comprise or consists of substitution of an amino acid at residue D71, Y85, N13, N4, D7, L9, V14, V15, D17 or V18. In one embodiment, the substitution may comprise or consists of substitution of an amino acid at residue D71 or Y85 The substitution may be with A. D71 designates the first conserved D in the PEBP domain adjacent to a V residue (V70 for the *Arabidopsis* sequence). As mentioned above, the numbering of the conserved amino acid residues targeted as used in this disclosure is based on the numbering of the *Arabidopsis* FT amino acid sequences. For example, Y85 designates the second conserved Y towards the N terminus of the PEBP domain. Combinations of the mutations listed above may also be used.

A peptide sequence expressed by said plant is shown in SEQ ID NO. 31 and 40. Homologous or orthologous sequences from other plants that carry the mutation at an equivalent position are within the scope of the invention.

In another aspect, the invention relates to a plant which may comprise and expressing a modified FT polynucleotide said polynucleotide encoding a modified polypeptide which may comprise an amino acid modification wherein said modification is a substitution and said substitution consists of or is selected from a substitution at one or more of the following residues as listed in table 1, particularly those listed in groups II-V and most preferred those in group V In one embodiment, substitution is with A. In one embodiment, the modification is a substitution and said substitution consists of or is selected from a substitution at V70 and/or T27, for example V70A and/or T27A.

In one embodiment, the plant also may comprise a regulatory sequence. This regulates expression of the polynucleotide in said plant. The sequence may be a promoter sequence, for example an endogenous promoter or a promoter that drives constitutive overexpression of a gene. Overexpression according to the invention means that the transgene is expressed at a level that is higher than expression driven by its endogenous promoter. For example, overexpression may be carried out using a strong promoter, such as the cauliflower mosaic virus promoter (CaMV35S), the rice actin promoter or the maize ubiquitin promoter or any promoter that gives enhanced expression. An inducible promoter, such as a stress-inducible promoter, for example the RubisCO small subunit promoter, or an ethylene, propylene, steroid or ethanol responsive promoter or a heat shock promoter may also be used. Also envisaged is ectopic expression, i.e. gene expression in a tissue in which it is normally not expressed. Alternatively, enhanced or increased expression may be achieved by using transcription or translation enhancers or activators and may incorporate enhancers into the gene to further increase expression. This list is not considered limiting as the skilled person will be able to select a suitable promoter that is capable of driving sufficient expression of the gene to result in the production of the modified protein.

The invention also extends to harvestable parts of modified plants described herein such as, but not limited to seeds, leaves, fruits, flowers, stems, roots, rhizomes, tubers, and bulbs, which harvestable parts comprise a recombinant nucleic acid encoding a modified FT polypeptide. The invention furthermore relates to products derived, preferably directly derived, from a harvestable part of such a plant, such as dry pellets or powders, oil, fat and fatty acids, starch or proteins.

In another aspect, the invention relates to a method for producing a plant as disclosed herein which may comprise introducing and expressing a modified FT polynucleotide in said plant wherein the polynucleotide encodes a modified polypeptide which may comprise an amino acid modification. In one embodiment, the invention thus relates to a method for producing a plant that produces more flowers and has increased fruit or seed production which may comprise introducing and expressing a modified FT polynucleotide in said plant wherein the polynucleotide encodes a modified polypeptide which may comprise an amino acid modification. Preferably, a modified FT polynucleotide encodes a modified polypeptide wherein V70 or T27 or both are replaced with another amino acid.

In another aspect, the invention relates to a method for increasing flowering and seed production in a plant which may comprise introducing and expressing a modified FT polynucleotide in said plant wherein the polynucleotide encodes a modified polypeptide which may comprise an amino acid modification. Preferably, the modified FT polynucleotide encodes a modified polypeptide wherein V70 and/or T27 is replaced with another amino acid.

The sequence which may comprise a modified FT polynucleotide sequence as described herein may further comprise a selectable marker that may be associated with the heterologous nucleic acid sequence, i.e., the structural gene operably linked to a promoter. As used herein, the term "marker" refers to a gene encoding a trait or a phenotype which permits the selection of, or the screening for, a plant or plant cell containing the marker. The marker gene may be an antibiotic resistance gene whereby the appropriate antibiotic may be used to select for transformed cells from among cells that are not transformed. Alternatively, the marker gene may be a herbicide resistance gene. Suitable markers will be known to those of skill in the art.

A skilled person will appreciate that to carry out the methods of the invention, a plant is transformed with a vector which may comprise the sequence of interest. Such vectors are disclosed herein. The details of the construction of the vectors that may be used are known to those skilled in the art of plant genetic engineering. The heterologous nucleic acid sequences utilized in the present invention may, for example, be introduced into plant cells using Ti plasmids, root-inducing (Ri) plasmids, or plant virus vectors, such as PVX.

The transformation of plants in accordance with the invention, i.e. the alteration of the genotype of a host plant by the introduction of a heterologous nucleic acid sequence, may be carried out in essentially any of the various ways known to those skilled in the art of plant molecular biology. Examples of transformation include infection by Agrobacterium, for example by infecting plant cells, an explant, a meristem or a seed, with transformed Agrobacterium tumefaciens. Under appropriate conditions known to those skilled in the art, the transformed plant cells are grown to form shoots, roots, and develop further into plants. Another example is transfection using a viral vector, such as the PVX vector system as shown herein, electroporation or particle bombardment. This list is non limiting as the skilled person will be able to use a suitable system.

Many Arabidopsis homologues and orthologues have been identified and a non-limited selection of these is shown in table 2 below.

TABLE 2

| Plant | FT gene |
| --- | --- |
| Arabidopsis | FT |
| Soybean | FT1 |
| Rice | OsFTL1, OsFT2 (Hd3a), OsFTL3 |
| Barley | HvFT1-HvFT5, VRN3 |
| Poplar | PtFT2 |
| Wheat | VRN3, TaFT |
| Tomato | SFT |
| Cucurbit | Cm-FTL1/2 |
| Maize | ZCN |
| Brassica | BnFT |
| Citrus | CiFT |
| Malus | MdFT1, MdFT2 |
| Vitis | VvFLT |
| Spruce | PaFT4 |
| Garden pea | PsFTL |
| Medicago | MtFTLa, MtFTLb, MtFTLc |
| Chenopodium | CrFTL1, CrFTL2 |
| Pharbitis nil | PnFT2 |

As shown herein, the plant according to the different aspects of the invention may be tobacco or barley. The inventors have shown that a modified gene sequence derived from the Arabidopsis FT gene may direct the expression of a modified FT protein in tobacco and induce an altered phenotype compared to the wild type. The skilled person would know that the invention is not limited to tobacco or barley which are used as a models plant in the experiments to illustrate the invention. Bearing in mind that the FT locus is conserved in many plant species, the skilled person would know that any monocot or dicot plant may be used according to the invention.

A dicot plant may be selected from the families including, but not limited to Asteraceae, Brassicaceae (eg Brassica napus), Chenopodiaceae, Cucurbitaceae, Leguminosae (Caesalpiniaceae, Aesalpiniaceae Mimosaceae, Papilionaceae or Fabaceae), Malvaceae, Rosaceae or Solanaceae. For example, the plant may be selected from lettuce, sunflower, Arabidopsis, broccoli, spinach, water melon, squash, cabbage, tomato, potato, capsicum, tobacco, cotton, okra, apple, rose, strawberry, alfalfa, bean, soybean, field (fava) bean, pea, lentil, peanut, chickpea, apricots, pears, peach, grape vine or citrus species. In one embodiment, the plant is oilseed rape.

Also included are biofuel and bioenergy crops such as rape/canola, linseed, lupin and willow, poplar, poplar hybrids, switchgrass, Miscanthus or gymnosperms, such as loblolly pine. Also included are crops for silage (maize), grazing or fodder (grasses, clover, sanfoin, alfalfa), fibres (e.g. cotton, flax), building materials (e.g. pine, oak), pulping (e.g. poplar), feeder stocks for the chemical industry (e.g. high erucic acid oil seed rape, linseed) and for amenity purposes (e.g. turf grasses for golf courses), ornamentals for public and private gardens (e.g. snapdragon, petunia, roses, geranium, Nicotiana sp.) and plants and cut flowers for the home (African violets, Begonias, chrysanthemums, geraniums, Coleus spider plants, Dracaena, rubber plant).

A monocot plant may, for example, be selected from the families Arecaceae, Amaryllidaceae or Poaceae. For example, the plant may be a cereal crop, such as wheat, rice, barley, maize, oat sorghum, rye, onion, leek, millet, buckwheat, turf grass, Italian rye grass, switchgrass, Miscanthus, sugarcane or Festuca species.

Preferably, the plant according to the different aspects of the invention is a crop plant. By crop plant is meant any plant which is grown on a commercial scale for human or animal consumption or use or other non-food/feed use.

Preferred plants are maize, wheat, rice, oilseed rape, sorghum, soybean, potato, tomato, barley, pea, bean, field bean, cotton, lettuce, broccoli or other vegetable brassicas or poplar. In another embodiment, the plant may be selected from the plants shown in table 1 and may express a modified endogenous FT gene based on the endogenous gene identified in table 1.

In one embodiment, the plant may be used for biofuel production.

The modified gene or polypeptide that is expressed in the plant according to the different aspects of the invention may be an exogenous gene, such as a modified *Arabidopsis* FT, expressed in a different plant species. Preferred plants are detailed above. Alternatively, the invention also relates to using a modified gene based on the endogenous FT gene. The endogenous FT gene is a FT *Arabidopsis* homologue or orthologue. Such genes are specified herein and known in the art. The modified polypeptide or gene encodes an altered protein as set forth herein and is introduced and expressed or overexpressed in the plant. Preferred plants are detailed above.

In another aspect, the invention provides an isolated modified FT nucleic acid sequence encoding a modified FT polypeptide which may comprise an amino acid modification. The modification may be a deletion, addition or substitution. Preferably, the modification is a substitution. The isolated modified nucleic acid sequence is selected from a sequence encoding a polypeptide which may comprise a substitution at one of the following residues or a combination thereof: T27, V70, D73, R119, R173, D71, L67, S78 Q140 or FTG16, FTL19, FTF22, FTK29 or FTV30. For example, the polypeptide may have a single substitution at these residues. Also envisaged is a modified polypeptide wherein the residue Y85 is replaced with A.

In one embodiment, the modified polypeptide has a single amino acid substitution selected from the substitutions above. In a preferred embodiment, the modified nucleic acid sequence encodes a polypeptide which may comprise a substitution at residue V70 or T27 or both. A skilled person will appreciate that to achieve the amino acid substitutions above, the corresponding codon must be altered and due to the degenerate code of the DNA, more than one alteration of the codon may be possible to generate the desired substitution.

A sequence or vector described herein encoding a modified FT protein is introduced as a transgene into the plant. This may be carried out by various methods as known in the field of plant genetic engineering, for example using transformation with *Agrobacterium*, PVX or particle bombardment.

In another aspect, the invention relates to a vector which may comprise a modified nucleic acid sequence that encodes a polypeptide as described herein. In a further aspect, the invention relates to a plant cell transformed with a vector or a gene sequence as described herein. Specifically, the invention relates to a host cell expressing a modified protein having a substitution at position V70 or T27 or both. The plant cell may be a cell of a monocot or dicot plant as further defined herein. Also within the scope of the invention is the use of a modified nucleic acid sequence encoding a polypeptide as described herein to alter flowering time and/or quantity and/or seed/fruit yield in a plant. For example, a modified nucleic acid sequence encoding a polypeptide which may comprise a substitution of residue V70 or T27 or both may be used to induce more flowering and increase seed yield in a plant. This may be carried out using the methods described herein.

In a further aspect, the invention relates to a method for producing a mutant plant expressing an FT variant and which is characterised by one of the phenotypes described herein wherein said method uses mutagenesis and Targeting Induced Local Lesions in Genomes (TILLING) to target the gene expressing the FT polypeptide. According to this method, lines that carry a specific mutation are produced that has a known phenotypic effect. For example, mutagenesis is carried out using TILLING where traditional chemical mutagenesis is flowed by high-throughput screening for point mutations. This approach does thus not involve creating transgenic plants. The plants are screened for one of the phenotypes described herein, for example a plant that shows increased flowering and seed production. The FT locus is then analysed to identify a specific FT mutation responsible for the phenotype observed. Plants may be bred to obtain stable lines with the desired phenotype and carrying a mutation in the FT locus. Thus, in one embodiment, the invention relates to a method for producing a plant exhibiting an altered phenotype selected from:
(a) increased flowering
(b) increased flowering and increased fruit and/or seed production;
(b) no bolting and no flowering;
(c) normal bolting and delayed flowering
(d) normal bolting and no flowering
said method which may comprise mutagenising a plant population and screening progeny derived from said population for said phenotype, identifying a plant exhibiting said phenotype and screening said plant for one or more point mutation in the FT locus.

Thus in one embodiment, the method used to create and analyse mutations is targeting induced local lesions in genomes (TLLING), reviewed in Henikoff et al, 2004, Plant Physiology, 2004, 630-636. In this method, seeds are mutagenised with a chemical mutagen, for example EMS. The resulting M1 plants are self-fertilised and the M2 generation of individuals is used to prepare DNA samples for mutational screening. DNA samples are pooled and arrayed on microtiter plates and subjected to gene specific PCR. The PCR amplification products may be screened for mutations in the FT target gene using any method that identifies heteroduplexes between wild type and mutant genes. For example, but not limited to, denaturing high pressure liquid chromatography (dHPLC), constant denaturant capillary electrophoresis (CDCE), temperature gradient capillary electrophoresis (TGCE), or by fragmentation using chemical cleavage. Preferably the PCR amplification products are incubated with an endonuclease that preferentially cleaves mismatches in heteroduplexes between wild type and mutant sequences. Cleavage products are electrophoresed using an automated sequencing gel apparatus, and gel images are analyzed with the aid of a standard commercial image-processing program. Any primer specific to the FT gene may be utilized to amplify the FT genes within the pooled DNA sample. Preferably, the primer is designed to amplify the regions of the FT gene where useful mutations are most likely to arise, specifically in the areas of the FT gene that are highly conserved and/or confer activity. To facilitate detection of PCR products on a gel, the PCR primer may be labelled using any conventional labelling method.

Rapid high-throughput screening procedures thus allow the analysis of amplification products for identifying a mutation conferring the reduction or inactivation of the expression of the FT gene as compared to a corresponding non-mutagenised wild type plant. Once a mutation is identified in a gene of interest, the seeds of the M2 plant carrying that mutation are grown into adult M3 plants and screened for the phenotypic characteristics associated with the FT gene. Loss of and reduced function mutants with increased yield and increased expression during leaf senescence compared to a wild type control may thus be identified.

In another aspect, the invention relates to a method for identifying a mutant plant which may comprise an FT variant polynucleotide sequence which may comprise identifying a mutant phenotype as described herein and analysing the FT polynucleotide sequence.

EXAMPLES

Having generally described this invention herein above, the following examples are provided to further describe the invention, to enable those skilled in the art to practice the full scope of this invention, including its best mode. The specifics of the examples which follow should not, however, be construed as limiting on the invention, as those skilled in the art will appreciate that variations, modifications and permutations of the specific details disclosed herein may yield useful results which, although differing in specific details, are nonetheless encompassed within the scope of the appended claims and equivalents thereof.

Example 1

Cloning of the FT Gene

The *Arabidopsis* FT derivatives encoding $FT_{G172A}$, $FT_{R173A}$ and $FT_{R174A}$ were amplified by PCR using the corresponding sets of primers A and D (FIG. 2) and the plasmid PVX/FT carrying the wild type FT gene as the template[12]. PCR mixtures (50 µl) contained 5 µl of 10× reaction buffer (Promega), 0.2 mM dNTPs (dATP, dGTP, dCTP and dTTP), 15 pmole of each primer, 1.25 units of pfu DNA polymerase (Promega) and 50 ng of template DNA. The resulting PCR products were purified using the QIAGEN Quick PCR Purification Kit, digested with ClaI and EagI, and then cloned into the ClaI/EagI sites of the PVX-based gene expression vectors[12].

All other FT derivatives (FIG. 2) were obtained by overlapping extension PCR. Each case involved designing two mutagenic primers B and C (FIG. 2) that contained specific mutations and were partially complementary to each other. Two separate PCR reactions (5 µl of 10× reaction buffer (Promega), 0.2 mM dNTPs (dATP, dGTP, dCTP and dTTP), 15 pmole of each of primers A and B or C and D, 1.25 units of pfu DNA polymerase (Promega) and 50 ng of template DNA) were performed to generate the 5'- and 3'-portions of the FT gene. The full-length FT derivative was then amplified through a third PCR (5 µl of 10× reaction buffer (Promega), 0.2 mM dNTPs (dATP, dGTP, dCTP and dTTP), 15 pmole of primer A and D, 1.25 units of pfu DNA polymerase (Promega) and 50 ng of the 5'- and 3'-portions of FT gene PCR products), purified, restriction enzymes-digested, and cloned into PVX to produce each of the corresponding expression vectors (FIG. 2a) as described above. The integrity of all recombinant clones and the presence of mutations were confirmed by sequencing.

Example 2

Modification of the FT Gene

To modify the 5'—(i.e. any nucleotide in the first 100 nucleotides) or 3'—(i.e. any nucleotide in the last 100 nucleotides) end of the FT gene, specific primers (30-110 nucleotides) having substitution of the codon for a chosen amino acid with the triple-nucleotides coding for alanine were chemically synthesised. Of course, using this methodology, other substitute amino acids may be utilized and the mutants thus produced are tested in the same fashion to that described below. The mutagenic primer was used along with either primer A or D (FIG. 2A) in PCRs as described in Example 1 in order to introduce specific modifications into the FT gene.

To introduce nucleotide changes into the middle part (i.e. nucleotide 101-429) of the FT gene, two partially complementary primers B and C (FIG. 2) were synthesised. Nucleotide changes were introduced into both primers in order to substitute the codon for the selected amino for mutation with the triple-nucleotide coding for alanine. The two mutagenic primers coupled with either primer A or D were used in the overlapping extension PCRs as described in Example 1 to introduce specific modifications into the FT gene.

Example 3

Expression of the Modified Gene in Plants

RNA transcripts from each recombinant PVX vector (FIG. 2) were produced by in vitro run-off transcription[12]. A typical in vitro transcription reaction (50 µl containing 5 µl of 10× buffer (Biolabs), 40 units of RNasin (Promega), 2 mM each of ATP, CTP, UTP and GTP, 0.5 mM $m^7GpppG$ (Biolabs), 2.5 µg of SpeI-linearised vector DNA, and 200 units of T7 RNA polymerase) was incubated at 37° C. for 1 hr. RNA transcripts were further treated with 1 unit of RNase-free DNase (Promega) at 37° C. for 30 min and then mechanically inoculated on the plants at 5 to 6 leaf stage. Young short-day (SD) *Nicotiana* tabacum Maryland Mammoth (MM) plants were maintained in insect-free glasshouses at 25° C. with continuous lighting to give a long-day (LD, 16-hr) photoperiod. Viral ectopic over-expression of the wild type and modified FT genes was analysed both at the RNA and the protein levels as previously described[12], and viral delivery of the wild type and modified FT genes was confirmed by sequencing.

Example 4

Analysis of Plants for Altered Phenotypes

Virus-treated SD MM plants developed virus-associated phenotypes including chlorotic lesions on inoculated leaves and mild chlorosis on young leaves after 7 to 14 days post-inoculation (dpi). Plants started to shoot at approx. 20 dpi and flowered at approx. 35 dpi if they were treated with a recombinant virus that expressed the wild-type *Arabidopsis* FT gene or its functional alleles. Plant growths (bolting) were measured weekly. Development of floral buds, flowers and seedpods were routinely checked and photographically recorded with a Nikon digital CoolPix 995 camera. Numbers of buds, fully-opened flowers and seedpods were counted. Seedpods were then collected, the amounts of seeds were weighted, and seeds were tested for germination. Phenotypes in terms of bolting, flowering time, numbers of flowers seedpods per plant which were affected by the viral ectopic expression of various FT mutants were compared to that of plants expressing the wild-type *Arabidopsis* FT.

Example 5

Transformation of Plants with the Modified Gene

The function-enhanced FT mutant $FT_{V70A}$ represents a novel gene that may have great potential in agricultural biotechnology. This is confirmed by transforming crop plants with the modified FT gene and analysing whether expression of $FT_{V70A}$ in crops induces similar phenotypes to those obtained in tobacco, i.e. increased flowering, increased flower number and increased fruit and/or seed yield. To this end, three expression cassettes (FIG. 6) are constructed for transformation of barley using a well-established transformation protocol[16]. This work is extended to crops including but not limited rice, wheat, maize, cotton, tomato, soybean, and brassicas, as well as horticultural and fruit crops, and ornamental species. Moreover, the valine residue which was substituted with alanine in $FT_{V70A}$ was found to be conserved among *Arabidopsis* FT and its orthologs in rice, barley, wheat and other species. Therefore, mutation of these amino acids in these FT orthologs with Alanine is predicted to enhance their biological function to trigger early flowering, increase floret number, and enhance kernel (seed) production through plant transformation.

Example 6

Analysis of Transformants for Altered Phenotypes

Figure 5:
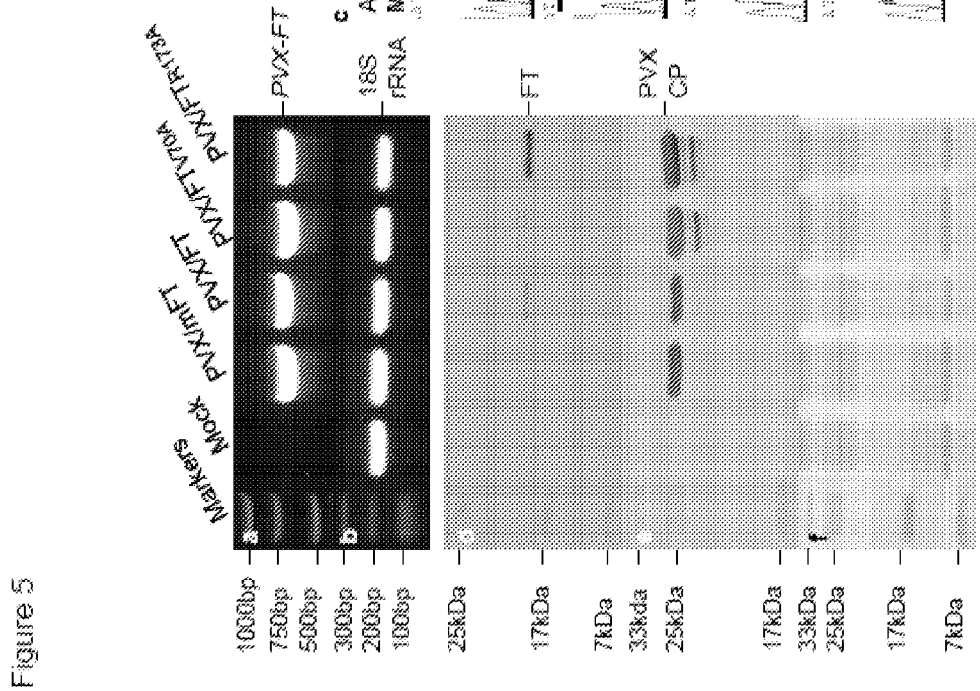
FIG. 5 Molecular analysis of FTV70A expression. (a-c) Detection of viral transient FT RNA. Viral transient FT RNA (a) and 18S rRNA (b) were detected in systemic young leaves by semi-quantitative RT-PCR. Total RNA samples were extracted from young leaves collected from plants mock-inoculated or inoculated with the PVX-based gene expression vectors at 5-wpi, pre-treated with RNase-free DNase, and used for RT-PCR detection as previously described[12]. RT-PCR products were sequenced to confirm the modified sequences (c).
Figure 13:
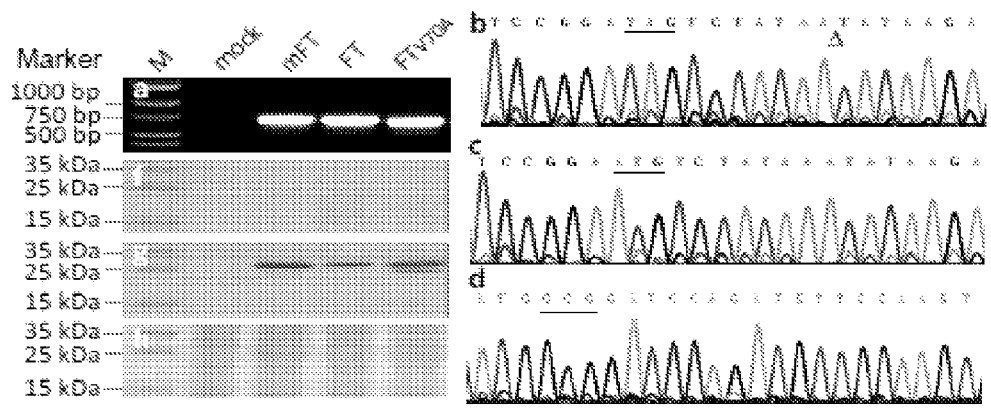
FIG. 13 Detection of viral transient expression of FT gene. (a) RT-PCR assay of viral transient FT gene in MM plants with mock inoculation (mock) or treated with PVX/mFT (mFT), PVX/FT (FT) or PVX/FTV70A (V70A). (b-d) Direct sequencing of viral transient FT-specific RT-PCR products confirms the recombinant viruses maintained the non-sense (underlined) and deletion (A) double mutations in mFT, wild-type FT (start codon ATG is underlined) or sense mutation (underlined) in FTV70A during the course of experiments.
Figure 14:
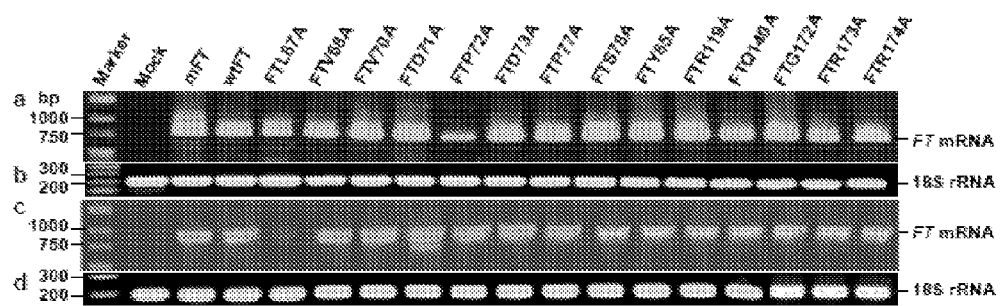
FIG. 14A-D RT-PCR Viral delivery and expression of *Arabidopsis* FT in SD MM tobacco plants. Detection of viral transient FT RNA (a, c) and 18S rRNA (b, d) in both inoculated (a, b) and systemic young (c, d) leaves by RT-PCR using primers PP82 and PP83 [Li C, Zhang K, Zeng X, Jackson S, Zhou Y and Hong Y (2009) A cis element within Flowering Locus T mRNA determines its mobility and facilitates trafficking of heterologous viral RNA. J Virol 83: 3540-3548].
Figure 15A:
Figure 15B:
Figure 15C:
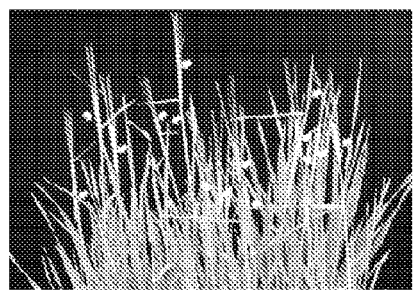
Figure 15D:
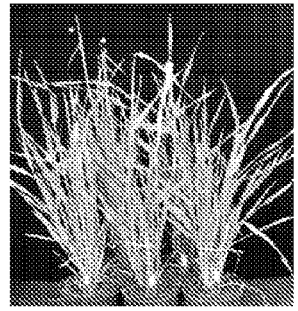
Figure 15E:
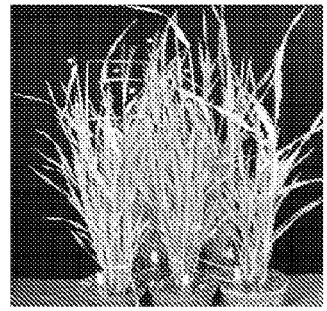
Figure 15F:
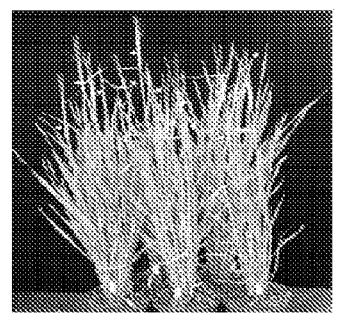
Figure 16:
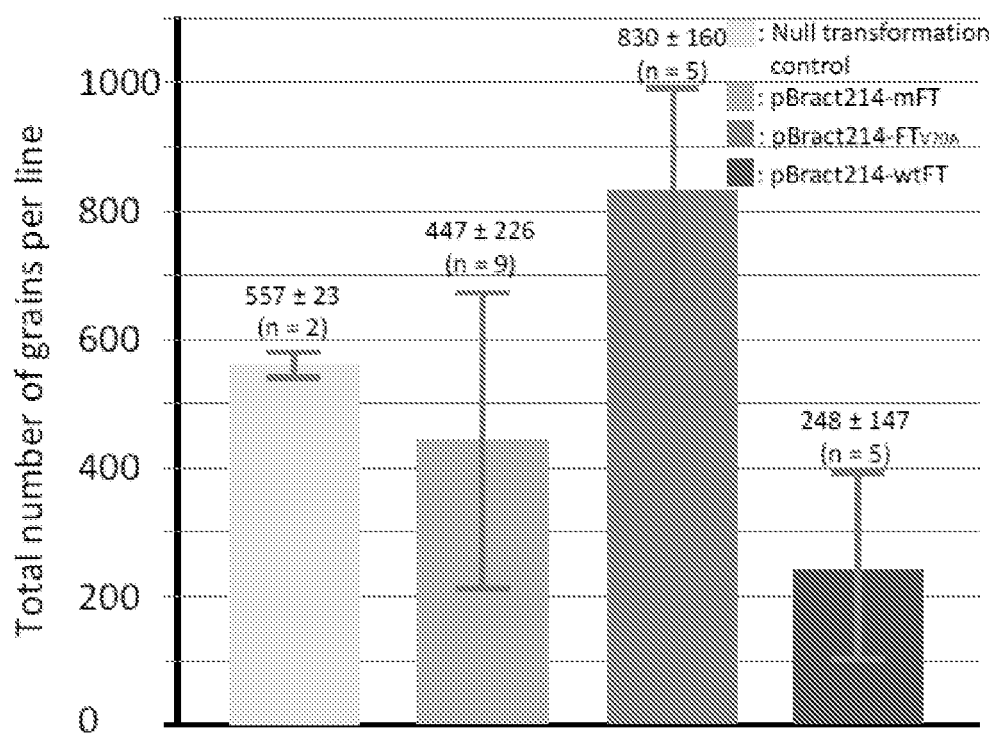
Figure 17:
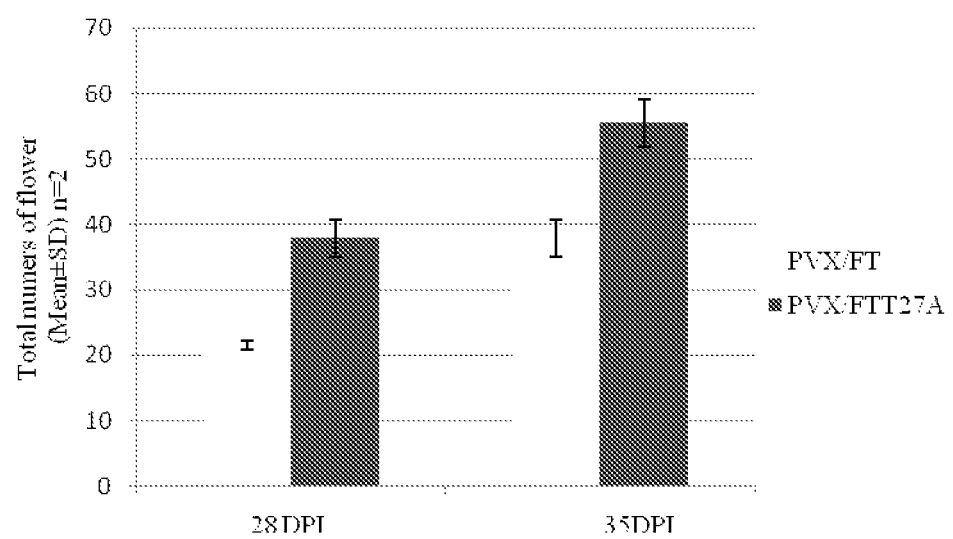
FIG. 17 $FT_{T27A}$ produces more flowers than FT in MM plants in SD.

Viral delivery of wild-type and mutated FT mRNA was readily detected in systemic leaves of PVX-treated MM tobacco plants by RT-PCR (FIG. 5a, b), indicating that an equivalent amount of FT mRNA was expressed from each of the corresponding recombinant viruses in the tested plants. Moreover, direct sequencing of the specific RT-PCR products demonstrated that the modifications introduced into the FT gene were stably maintained during the course of the experiments (FIG. 5c). Using an antiserum specifically raised against FT peptides, Applicants detected a single band of approx. 20 kDa corresponding to the predicted size of the FT protein expressed in plants inoculated with PVX/FT and an R173A "loss-of-function" FT protein variant (Table 1) in plants inoculated with $PVX/FT_{R173A}$ (FIG. 2a; FIG. 5d). Surprisingly, in plants inoculated with $PVX/FT_{V70A}$, two forms of $FT_{V70A}$ were consistently found, suggesting that $FT_{V70A}$ may have undergone post-translational modification and possibly that this modification may be required for the novel functionality of this synthetic protein. Consistent with the RT-PCR assays showing equivalent amounts of FT mRNA in the inoculated plants, similar amounts of the PVX CP were also detected (FIG. 5e, f), demonstrating that the PVX-based expression system is able to deliver equal amounts of FT mRNA and its protein products in all inoculated MM tobacco plants.

Phenotypes (growth, flowering time, flower number, seed yield and productivity) of primary transformants are compared with that of plants transformed with control gene expression cassettes (FIG. 6). Copy numbers of transgenes in each transgenic line is determined and lines with a single copy of the relevant transgenes are selected for further analysis. Transgene expression is analysed at the RNA and protein levels, which are then correlated with the phenotypic changes among transgenic lines transformed with the three different gene expression cassettes (FIG. 6). It is anticipated that (1) increases in floral numbers is in particular beneficial to horticultural industry for breeding novel flower plants; and (2) increases in productivity is particularly beneficial to agriculture, food and biotechnology for breeding novel crops for high yields and for biofuel production.

Example 7

Possible Implications of the Function-Enhanced $Ft_{V70A}$ in Molecular Breeding of Novel Crops Applicants' data demonstrate that the V70A substitution in the FT protein is responsible for the enhanced biological activity of $FT_{V70A}$, enabling it to trigger flowering and cause increased flower numbers and seed yield. This finding is important in terms of engineering the FT protein for enhanced crop productivity. In addition, Applicants' virus-based floral induction system revealed a number of other potentially useful alleles of FT that confer different flowering responses (Table 1). For instance, over-expression of Group IV mutants (i.e. no bolting and no flowering) may have a dominant negative effect on plants, e.g. lettuce, so that such crops remain vegetative growth. Another potential application of the Group IV mutants may be found in biomass crops for example to avoid energy being diverted into flowering processes (bolting and flowering), in particular for vegetatively species where a flowering/seed phase is not necessary for agricultural cultivation (e.g. sugar cane). The Group IV mutants (no bolting, no flowering) could also have uses in fertility control, by preventing flowering altogether when flowering is not required, for example sugar beet, turfgrasss etc.

Knowledge of such an allelic series that confers a range of flowering characteristics is useful to molecular plant breeders, who, based on the present disclosure, could produce lines carrying a specific mutation that has a known phenotypic effect through targeted molecular breeding approaches, e.g. by screening for a specific FT mutation in TILLING populations. Another potential application is the use of non seed-borne viral vectors expressing FT or $FT_{V70A}$ to promote flowering and seed production in breeding programmes or in recalcitrant plant species in germplasm collections. Furthermore, the pools of FT mutants, in particular, the non-flowering "loss-of-function" alleles in group III and IV (Table 1), represent a unique resource for dissecting the molecular domains of the FT protein that are responsible for the long-distance movement and the cell-autonomous floral induction.

Example 8

Quantitative Real-Time PCR for Determining Transgene Copy Number

Quantitative real-time PCR was carried out using Hyg gene and CO2 (Constans-like, AF490469) gene specific primers and probes [Bartlett J G, Alves S C, Smedley M, Snape J W, Harwood W A (2008) High-throughput *Agrobacterium*-mediated barley transformation. Plant Methods, 4: 22]. Primers were designed to the target sequences using Applied Biosystems software Primer Express, with the TaqMan Probe and Primer design module (see below). The reactions used Thermo ABGene Absolute QPCR Rox Mix (Cat number AB 1139). The Hyg gene and the CO2 gene were assayed in multiplex. The probes and primer final concentrations were 200 nM (Hyg) or 100 nM (CO2). The assay contained 5 µl of DNA solution, and was optimised for final DNA concentrations 1 to 10 ng/μl (5 to 50 ng DNA in the assay). PCRs were carried out in an Applied Biosystems AB17900 equipped with a 384 place plate. The detectors used were FAM-TAMRA and VIC-TAMRA with Rox internal passive reference, and no 9600 emulation. The PCR cycling conditions were 95° C. 15 minutes (enzyme activation), 40 cycles of 95° C. 15 seconds, 60° C. 60 seconds. Each sample was analysed twice.

| Name | Sequence | Final concentration in PCR |
|---|---|---|
| HvHygF3 SEQ ID No. 46 | GGATTTCGGCTCCAACAATG | 200 nM |
| HvHygR2 SEQ ID No. 47 | TATTGGGAATCCCCGAACATC | 200 nM |
| HvCon2F1 SEQ ID No. 48 | TGCTAACCGTGTGGCATCAC | 100 nM |
| HvCon2R1 SEQ ID No. 49 | GGTACATAGTGCTGCTGCATCTG | 100 nM |
| HvHygP SEQ ID No. 50 | Fam-CAGCGGTCATTGACTGGAG CGAGG-Tamra | 200 nM |
| HvCon2P SEQ ID No. 51 | VIC-CATGAGCGTGTGCGTGTCT GCG-TAMRA | 100 nM |

After PCR the Cycle Threshold (CT) values were obtained using the Applied Biosystems SDS software, after adjusting the background subtraction and threshold values, so that all amplification curves were close to mid-log amplification. The delta Ct value (Ct of Hyg minus the Ct of CO2) was calculated for each sample. The samples were sorted by delta Ct, those with high ΔCt values have low copy numbers, and those with low ΔCt have high copy numbers of the Hyg gene.

Example 9

Plant Material and Immature Embryo Isolation

Table 3 below shows primer sequences (SEQ ID No. 52-78)

TABLE 3

Table 3 Primer sequences

| Primer | Sequence (5'-3') | SEQ ID NO: |
|---|---|---|
| PP331 | AAGATCATCGATGTCTATAAATATAAGAGACCCTC | 52 |
| PP332 | AGAAGCCGGCCGAAGTCTTCTTCCTCCGCAGCCAC | 53 |
| PP527 | TCTGGATCCACCATAACCGCAGTATAGAAG | 54 |
| PP528 | CTTCTATACTGCGGTTATGGTGGATCCAGA | 55 |
| PP529 | TCTGGATCCACCATCGCCAAAGTATAGAAG | 56 |
| PP530 | CTTCTATACTTTGGCGATGGTGGATCCAGA | 57 |
| PP531 | TCTGGATCCGCCATAACCAAAGTATAGAAG | 58 |
| PP532 | CTTCTATACTTTGGTTATGGCGGATCCAGA | 59 |
| PP533 | ACTTGGAACATCTGGCGCCACCATAACCAAAG | 60 |

TABLE 3-continued

Table 3 Primer sequences

| Primer | Sequence (5'-3') | SEQ ID NO: |
|---|---|---|
| PP534 | CTTTGGTTATGGTGGCGCCAGATGTTCCAAGT | 61 |
| PP535 | ACTTGGAACATCCGCATCCACCATAACCAAAG | 62 |
| PP536 | CTTTGGTTATGGTGGATGCGGATGTTCCAAGT | 63 |
| PP537 | ACTTGGAACCGCTGGATCCACCATAACCAAAG | 64 |
| PP538 | CTTTGGTTATGGTGGATCCAGCGGTTCCAAGT | 65 |
| PP539 | CTCGGAGGTGAGGGTTGCTCGCACTTGGAACA | 66 |
| PP540 | TGTTCCAAGTGCGAGCAACCCTCACCTCCGAG | 67 |
| PP541 | CTCGGAGGTGAGGGTTCGCAGGACTTGGAACA | 68 |
| PP542 | TGTTCCAAGTCCTGCGAACCCTCACCTCCGAG | 69 |
| PP543 | ACCAACCAATGGAGCGCTTCTCGGAGGTGAG | 70 |
| PP544 | CTCACCTCCGAGAAGCGCTCCATTGGTTGGT | 71 |
| PP545 | TATAAACACGACCGCATGAATTCCTGCAGTG | 72 |
| PP546 | CACTGCAGGAATTCATGCGGTCGTGTTTATA | 73 |
| PP547 | TGTTGAAGTTCGCGCGCCACCCTGGTGCATAC | 74 |
| PP548 | GTATGCACCAGGGTGGCGCGCGAACTTCAACA | 75 |
| PP549 | GGAAGACGGCCGCTAAAGTCTTCTCGCTCCGCAGC | 76 |
| PP551 | GGAAGACGGCCGCTAAAGTCTCGCTCCTCCGCAGC | 77 |
| PP552 | GGAAGACGGCCGCTAAAGCGCTCTTCCTCCGCAGC | 78 |

Example 10

Plasmids and Bacterial Strain

Agrobacterium strain AGL1 containing pBract vectors was used in all experiments. All pBract vectors are based on pGreen [Hellens R P, Edwards E A, Leyland N R, Bean S, Mullineaux P M: pGreen: a versatile and flexible binary Ti vector for Agrobacterium-mediated plant transformation. Plant Mol Biol 2000, 42:819-832] and therefore need to be co-transformed into Agrobacterium with the helper plasmid pSoup. To enable the small size of pGreen, the pSa origin of replication required for replication in Agrobacterium, is separated into its' two distinct functions. The replication origin (ori) is present on pGreen, and the trans-acting replicase gene (RepA) is present on pSoup. Both vectors are required in Agrobacterium for pGreen to replicate. pBract vector DNA and pSoup DNA were concurrently transferred to AGL1 via electroporation.

Example 11

Agrobacterium-Mediated Transformation

The method of Tingay et al. [Tingay S, McElroy D, Kalla R, Fieg S, Wang M, Thornton S, Brettell R: Agrobacterium tumefaciens-mediated barley transformation. Plant J 1997, 11:1369-1376] was used to prepare a standard Agrobacterium inoculum for transformation. A 400 μl aliquot of standard inoculum was removed from −80° C. storage, added to 10 ml of MG/L [Bartlett J G, Alves S C, Smedley M, Snape J W, Harwood W A (2008) High-throughput *Agrobacterium*-mediated barley transformation. Plant Methods, 4: 22] medium without antibiotics and incubated on a shaker at 180 rpm at 28° C. overnight. This full strength culture was used to inoculate the prepared immature embryos. A small drop of *Agrobacterium* suspension was added to each of the immature embryos on a plate. The plate was then tilted to allow any excess *Agrobacterium* suspension to run off. Immature embryos were then gently dragged across the surface of the medium (to remove excess *Agrobacterium*) before being transferred to a fresh CI plate, scutellum side down. Embryos were co-cultivated for 3 days at 23-24° C. in the dark.

Example 12

Selection of Transformed Plants

After co-cultivation, embryos were transferred to fresh CI plates containing 50 mg $l^{-1}$ hygromycin, 160 mg $l^{-1}$ Timentin (Duchefa) and 1.25 mg $l^{-1}$ $CuSO_4.5H_2O$. Embryos were sub-cultured onto fresh selection plates every 2 weeks and kept in the dark at 24° C. After 4-6 weeks, embryos were transferred to transition medium (T) containing 2.7 g $l^{-1}$ Murashige & Skoog modified plant salt base (without $NH_4NO_3$) (Duchefa), 20 g $l^{-1}$ Maltose, 165 mg $l^{-1}$ $NH_4NO_3$, 750 mg $l^{-1}$ Glutamine, 100 mg $l^{-1}$ Myo-inositol, 0.4 mg $l^{-1}$ Thiamine HCl, 1.25 mg $l^{-1}$ $CuSO_4.5H_2O$, 2.5 mg $l^{-1}$ 2,4-Dichlorophenoxy acetic acid (2,4-D) (Duchefa), 0.1 mg $l^{-1}$ 6-Benzylaminopurine (BAP), 3.5 g $l^{-1}$ Phytagel, 50 mg $l^{-1}$ Hygromycin and 160 mg $l^{-1}$ Timentin in low light. After a further 2 weeks, embryo derived callus was transferred to regeneration medium in full light at 24° C., keeping all callus from a single embryo together. Regeneration medium was the same as the transition medium but without additional copper, 2,4-D or BAP. Once regenerated plants had shoots of 2-3 cm in length they were transferred to glass culture tubes containing CI medium, without dicamba or any other growth regulators but still containing 50 mg $l^{-1}$ hygromycin and 160 mg $l^{-1}$ Timentin. Transformed plants developed a strong root system in the hygromycin containing medium in 1-2 weeks and were then transferred to soil and grown under the same conditions as the donor plants.

Table 3 below shows primer sequences (SEQ ID No. 52-78)

TABLE 3

Table 2 Primer sequences

| Primer | Sequence (5'-3') |
|---|---|
| PP331 | AAGATCATCGATGTCTATAAATATAAGAGACCCTC |
| PP332 | AGAAGCCGGCCGAAGTCTTCTTCCTCCGCAGCCAC |
| PP527 | TCTGGATCCACCATAACCGCAGTATAGAAG |
| PP528 | CTTCTATACTGCGGTTATGGTGGATCCAGA |
| PP529 | TCTGGATCCACCATCGCCAAAGTATAGAAG |
| PP530 | CTTCTATACTTTGGCGATGGTGGATCCAGA |
| PP531 | TCTGGATCCGCCATAACCAAAGTATAGAAG |
| PP532 | CTTCTATACTTTGGTTATGGCGGATCCAGA |
| PP533 | ACTTGGAACATCTGGCGCCACCATAACCAAAG |
| PP534 | CTTTGGTTATGGTGGCGCCAGATGTTCCAAGT |
| PP535 | ACTTGGAACATCCGCATCCACCATAACCAAAG |
| PP536 | CTTTGGTTATGGTGGATGCGGATGTTCCAAGT |
| PP537 | ACTTGGAACCGCTGGATCCACCATAACCAAAG |
| PP538 | CTTTGGTTATGGTGGATCCAGCGGTTCCAAGT |
| PP539 | CTCGGAGGTGAGGGTTGCTCGCACTTGGAACA |
| PP540 | TGTTCCAAGTGCGAGCAACCCTCACCTCCGAG |
| PP541 | CTCGGAGGTGAGGGTTCGCAGGACTTGGAACA |
| PP542 | TGTTCCAAGTCCTGCGAACCCTCACCTCCGAG |
| PP543 | ACCAACCAATGGAGCGCTTCTCGGAGGTGAG |
| PP544 | CTCACCTCCGAGAAGCGCTCCATTGGTTGGT |
| PP545 | TATAAACACGACCGCATGAATTCCTGCAGTG |
| PP546 | CACTGCAGGAATTCATGCGGTCGTGTTTATA |
| PP547 | TGTTGAAGTTCGCGCGCCACCCTGGTGCATAC |
| PP548 | GTATGCACCAGGGTGGCGCGCGAACTTCAACA |
| PP549 | GGAAGACGGCCGCTAAAGTCTTCTCGCTCCGCAGC |
| PP551 | GGAAGACGGCCGCTAAAGTCTCGCTCCTCCGCAGC |
| PP552 | GGAAGACGGCCGCTAAAGCGCTCTTCCTCCGCAGC |

SEQUENCE LISTING

*Arabidopsis thaliana* FT nucleic acid sequence (wild type)
SEQ ID No 1
ATGTCTATAAATATAAGAGACCCTCTTATAGTAAGCAGAGTTGTTGGAGA
CGTTCTTGATCCGTTTAATAGATCAATCACTCTAAAGGTTACTTATGGCCA
AAGAGAGGTGACTAATGGCTTGGATCTAAGGCCTTCTCAGGTTCAAAACA
AGCCAAGAGTTGAGATTGGTGGAGAAGACCTCAGGAACTTCTATACTTTG
GTTATGGTGGATCCAGATGTTCCAAGTCCTAGCAACCCTCACCTCCGAGA
ATATCTCCATTGGTTGGTGACTGATATCCCTGCTACAACTGGAACAACCTT
TGGCAATGAGATTGTGTGTTACGAAAATCCAAGTCCCACTGCAGGAATTC
ATCGTGTCGTGTTTATATTGTTTCGACAGCTTGGCAGGCAAACAGTGTATG
CACCAGGGTGGCGCCAGAACTTCAACACTCGCGAGTTTGCTGAGATCTAC
AATCTCGGCCTTCCCGTGGCCGCAGTTTTCTACAATTGTCAGAGGGAGAG
TGGCTGCGGAGGAAGAAGACTTTAG -continued

*Arabidopsis thaliana* FT polypeptide (wild type) SEQ ID No 2
```
MSINIRDPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

GROUP I

*Arabidopsis thaliana* FT polypeptide FTV68A SEQ ID 3
```
MAINIRDPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTP72A SEQ ID 4
```
MAINIRDPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTP77A SEQ ID 5
```
MAINIRDPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTG172A SEQ ID 6
```
MAINIRDPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTR174A SEQ ID 7
```
MAINIRDPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTS2A SEQ ID 8
```
MAINIRDPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTI5A SEQ ID 9
```
MSINARDPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTR6A SEQ ID 10
```
MSINIADPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTP8A SEQ ID 11
```
MSINIRDALI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTV11A SEQ ID 12
```
MSINIRDPLI ASRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTS12A SEQ ID 13
```
MSINIRDPLI VARVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTR13A SEQ ID 14
```
MSINIRDPLI VSAVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

-continued

*Arabidopsis thaliana* FT polypeptide FTD20A SEQ ID 15
```
MSINIRDPLI VSRVVGDVLA PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                          175
```

*Arabidopsis thaliana* FT polypeptide FTP21A SEQ ID 16
```
MSINIRDPLI VSRVVGDVLD AFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                          175
```

*Arabidopsis thaliana* FT polypeptide FTN23A SEQ ID 17
```
MSINIRDPLI VSRVVGDVLD PFARSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                          175
```

*Arabidopsis thaliana* FT polypeptide FTR24A SEQ ID 18
```
MSINIRDPLI VSRVVGDVLD PFNASITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                          175
```

*Arabidopsis thaliana* FT polypeptide FTS25A SEQ ID 19
```
MSINIRDPLI VSRVVGDVLD PFNRAITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                          175
```

*Arabidopsis thaliana* FT polypeptide FTI26A SEQ ID 20
```
MSINIRDPLI VSRVVGDVLD PFNRSATLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                          175
```

*Arabidopsis thaliana* FT polypeptide FTL28A SEQ ID 21
```
MSINIRDPLI VSRVVGDVLD PFNRSITAKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                          175
```

*Arabidopsis thaliana* FT polypeptide FTT31A SEQ ID 22
```
MSINIRDPLI VSRVVGDVLD PFNRSITLKV AYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                          175
```

GROUP II

*Arabidopsis thaliana* FT polypeptide FTG16A SEQ ID 23
```
MSINIRDPLI VSRVVADVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                          175
```

*Arabidopsis thaliana* FT polypeptide FTL19A SEQ ID 24
```
MSINIRDPLI VSRVVGDVAD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                          175
```

*Arabidopsis thaliana* FT polypeptide FTF22A SEQ ID 25
```
MSINIRDPLI VSRVVGDVLD PANRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                          175
```

*Arabidopsis thaliana* FT polypeptide FTK29A SEQ ID 26
```
MSINIRDPLI VSRVVGDVLD PFNRSITLAV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                          175
```

*Arabidopsis thaliana* FT polypeptide FTV30A SEQ ID 27
```
MSINIRDPLI VSRVVGDVLD PFNRSITLKA TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                          175
```

*Arabidopsis thaliana* FT polypeptide FTL67A SEQ ID No 28
```
MSINIRDPLI VSRVVGDVLD PFNRSITLKV TYGQREVTNG LDLRPSQVQN  50
KPRVEIGGED LRNFYTAVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTS78A SEQ ID No 29
```
MSINIRDPLI VSRVVGDVLD PFNRSITLKV TYGQREVTNG LDLRPSQVQN  50
KPRVEIGGED LRNFYTLVMV DPDVPSPANP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTQ140A SEQ ID No 30
```
MSINIRDPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRA NFNTREFAEI 150
YNLGLPVAAV FYNCQRESGC GGRRL                           175
```

GROUP III

*Arabidopsis thaliana* FT polypeptide FTI3A SEQ ID 31
```
MSANIRDPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTN4A SEQ ID 32
```
MSIAIRDPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTD7A SEQ ID 33
```
MSINIRAPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTL9A SEQ ID 34
```
MSINIRDPAI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTV14A SEQ ID 35
```
MSINIRDPLI VSRAVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTV15A SEQ ID 36
```
MSINIRDPLI VSRVAGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTD17A SEQ ID 37
```
MSINIRDPLI VSRVVGAVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTV18A SEQ ID 38
```
MSINIRDPLI VSRVVGDALD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTD71A SEQ ID No 39
```
MSINIRDPLI VSRVVGDVLD PFNRSITLKV TYGQREVTNG LDLRPSQVQN  50
KPRVEIGGED LRNFYTLVMV APDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                           175
```

*Arabidopsis thaliana* FT polypeptide FTY85A SEQ ID No 40
```
MSINIRDPLI VSRVVGDVLD PFNRSITLKV TYGQREVTNG LDLRPSQVQN  50
KPRVEIGGED LRNFYTLVMV DPDVPSPSNP HLREALHWLV TDIPATTGTT 100
```

```
FGNEIVCYEN PSPTAGIHRV VFILFRQLGR QTVYAPGWRQ NFNTREFAEI 150
YNLGLPVAAV FYNCQRESGC GGRRL                         175
```

GROUP IV

```
Arabidopsis thaliana FT polypeptide FTD73A SEQ ID No 41
MSINIRDPLI VSRVVGDVLD PFNRSITLKV TYGQREVTNG LDLRPSQVQN  50
KPRVEIGGED LRNFYTLVMV DPAVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                         175

Arabidopsis thaliana FT polypeptide FTR119A SEQ ID No 42
MSINIRDPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHAV VFILFRQLGR QTVYAPGWRQ NFNTREFAEI 150
YNLGLPVAAV FYNCQRESGC GGRRL                         175

Arabidopsis thaliana FT polypeptide FTR173A SEQ ID No 43
MSINIRDPLI VSRVVGDVLD PFNRSITLKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGARL                         175
```

GROUP V

```
Arabidopsis thaliana FT polypeptide FTV70A SEQ ID No 44
MSINIRDPLI VSRVVGDVLD PFNRSITLKV TYGQREVTNG LDLRPSQVQN  50
KPRVEIGGED LRNFYTLVMA DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                         175

Arabidopsis thaliana FT polypeptide FTT27A SEQ ID 45
MSINIRDPLI VSRVVGDVLD PFNRSIALKV TYGQREVTNG LDLRPSQVQN  50
KPRVEIGGED LRNFYTLVMV DPDVPSPSNP HLREYLHWLV TDIPATTGTT 100
FGNEIVCYEN PSPTAGIHRV VFILFRQLGR QTVYAPGWRQ NFNTREFAEI 150
YNLGLPVAAV FYNCQRESGC GGRRL                         175
```

REFERENCES

1. Zeevaart, J. A. D. *Annu. Rev. Plant Physiol.* 27, 321-348 (1976).
2. Corbesier, L. & Coupland, G. *J. Exp. Bot.* 57, 3395-3403 (2006).
3. Tatada, S. & Goto, K. *Plant Cell* 15, 2856-2865 (2003).
4. Abe, M. et al. *Science* 309, 1052-1056 (2005).
5. An, H. et al. *Development* 131, 3615-3626 (2004).
6. Wigge, P. et al. *Science* 309, 1056-1059 (2005).
7. Corbesier, L. et al. *Science* 316, 1030-1033 (2007).
8. Giavalisco, P. et al. *Proteomics* 6, 896-909 (2006).
9. Lifschitz, E. et al. *PNAS* 103, 6398-6403 (2006).
10. Tamaki, S. et al. *Science* 316, 1033-1036 (2007).
11. Lin, M. K. et al. *Plant Cell* 19, 1488-1506 (2007).
12. Li, C. et al. *J. Virol.* 83, 3540-3548 (2009).
13. Takahashi, Y. et al. *PNAS* 106, 4555-4560 (2009).
14. Hanzawa, Y., Money, T. & Bradley, D. *PNAS* 102, 7748-7753 (2005).
15. Khush, G. S. *Nat. Rev. Genet.* 2, 815-822 (2001).
16. Tingay, et al. *Plant J.* 11, 1369-1376 (1997).
17. Ziegler, A. et al. Arch Virol DOI 10.1007/s00705-009-0468-8 (2009).

The invention is further described by the following numbered paragraphs:

1. A transgenic plant comprising and expressing a modified FT polynucleotide said polynucleotide encoding a modified polypeptide comprising an amino acid modification wherein said plant exhibits one of the following phenotypes:
   a) increased flowering and increased fruit and/or seed production;
   b) increased flowering
   c) no bolting and no flowering;
   d) normal bolting and delayed flowering provided that the amino acid modification does not comprise Y85H or
   e) normal bolting and no flowering.
2. A plant according to paragraph 1 wherein said plant exhibits increased flowering and increased fruit and/or seed production.
3. A plant according to paragraph 2 wherein said modification comprises or consists of an amino acid substitution at the second conserved V residue in the PEBP domain.
4. A plant according to paragraph 3 wherein said conserved V residue is V70 or a V at a homologous position.
5. A plant according to paragraph 2 wherein said modification comprises or consists of an amino acid substitution at T27 or at a homologous position.
6. A plant according to paragraph 1 wherein said plant exhibits no bolting and no flowering.
7. A plant according to paragraph 6 wherein said modification comprises or consists of an amino acid substitution selected from a substitution at one or more of the following residues: D73, R119 or R173.
8. A plant according to paragraph 1 wherein said plant exhibits normal bolting and delayed flowering provided that the amino acid modification does not comprise Y85H.
9. A plant according to paragraph 8 wherein said modification comprises or consists of an amino acid substitution selected from a substitution at one or more of the following residues: L67, S78 Q140, G16, L19, F22, K29 or V30.
10. A plant according to paragraph 1 wherein said plant exhibits normal bolting and no flowering.

11. A plant according to paragraph 10 wherein said modification comprises or consists of an amino acid substitution selected from a substitution at one or more of the following residues: D71 oY85, 13, N4, D7, L9, V14, V15, D17 or V18.
12. A plant according to any of paragraphs 1 to 11 wherein the amino acid substitution is with a neutral amino acid.
13. A plant according to paragraph 12 wherein the amino acid substitution is with Alanine.
14. A plant according to any of paragraphs 1 to 13 wherein the FT polynucleotide is operably linked to a regulatory sequence.
15. A plant according to paragraph 14 wherein said regulatory sequence is a promoter.
16. A plant according to any of paragraphs 1 to 15 wherein the plant is a monocot or dicot plant.
17. A plant according to paragraph 16 wherein said plant is a crop plant.
18. A plant according to paragraph 17 wherein said plant is selected from maize, wheat, rice, sorghum, soybean, sugar cane, sugar beet, forage grass, turfgrass, switchgrass, miscanthus, potato, tomato, barley, pea, bean, field bean, cotton, lettuce, sunflower, brassicas, such as canola, oilseed rape, or broccoli, or alfalfa, or poplar.
19. A plant according to any of paragraphs 1 to 18 wherein said modified FT polynucleotide is a modified endogenous polynucleotide.
20. A plant according to any of paragraphs 1 to 18 wherein said modified FT polynucleotide is a modified exogenous polynucleotide.
21. Plant tissue or harvestable material derived from a plant according to any of paragraphs 1 to 20.
22. A method for producing a plant as defined in any of paragraphs 1 to 20 comprising introducing and expressing a modified FT polynucleotide in said plant wherein the polynucleotide encodes a modified polypeptide comprising an amino acid modification.
23. A method for increasing flowering and seed and/or fruit production in a plant comprising introducing and expressing a modified FT polynucleotide in said plant wherein the polynucleotide encodes a modified polypeptide comprising an amino acid modification.
24. A method according to paragraph 23 wherein said modification comprises or consists of an amino acid substitution at residue V70 or T27 or both.
25. An isolated nucleic acid said nucleic acid encoding a modified polypeptide comprising an amino acid modification wherein said modification results in an altered phenotype when said nucleic acid is introduced in a plant wherein said phenotypes is selected from:
    a) increased flowering increased flowering and increased fruit and/or seed production;
    b) increased flowering;
    c) no bolting and no flowering;
    d) normal bolting and delayed flowering provided that the amino acid modification does not comprise Y85H or
    e) normal bolting and no flowering.
26. An isolated nucleic acid said nucleic acid encoding a modified polypeptide comprising an amino acid modification wherein said modification consists of or comprises a substitution of one or more of the following residues: T27, V70, D73, R119, R173, D71, L67, S78, Q140 or G16, L19, F22, K29 or FTV30.
27. An isolated nucleic acid according to paragraph 25 or 26 wherein said modification consists of or comprises a substitution at residue V70 or T27 or both.
28. An isolated nucleic acid according to paragraph 26 or 27 wherein the amino acid is substituted with A.
29. A vector comprising a nucleic acid as defined in any of paragraphs 25 to 28.
30. The use of a nucleic acid as defined in any of paragraphs 25 to 28 or a vector as defined in paragraph 29 to increase flowering and/or seed and or fruit production in a plant.
31. A plant comprising a nucleic acid as defined in any of paragraphs 25 to 28 or a vector as defined in paragraph 29.
32. A method for producing a plant exhibiting an altered phenotype selected from:
    a) increased flowering
    b) increased flowering and increased fruit and/or seed production;
    c) no bolting and no flowering;
    d) normal bolting and delayed flowering
    e) normal bolting and no flowering
        said method comprising mutagenising a plant population and screening progeny derived form said population for said phenotype, identifying a plant exhibiting said phenotype and screening said plant for one or more point mutation in the FT locus.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A modified plant comprising and expressing a modified Flowering Locus T (FT) polynucleotide, said polynucleotide encoding a modified polypeptide comprising an amino acid modification in SEQ ID NO: 2, wherein said plant exhibits increased fruit and/or seed production, and wherein said modification comprises an amino acid substitution at V70 and/or an amino acid substitution at T27.

2. A plant according to claim 1, wherein the amino acid substitution is with a neutral amino acid.

3. A plant according to claim 2, wherein the amino acid substitution is with Alanine.

4. A plant according to claim 1, wherein the FT polynucleotide is operably linked to a regulatory sequence.

5. A plant according to claim 4, wherein said regulatory sequence is a promoter.

6. A plant according to claim 1, wherein the plant is a monocot or dicot plant.

7. A plant according to claim 6, wherein said plant is a crop plant.

8. A plant according to claim 7, wherein said plant is selected from the group consisting of maize, wheat, rice, sorghum, soybean, sugar cane, sugar beet, forage grass, turfgrass, switchgrass, miscanthus, potato, tomato, barley, pea, bean, field bean, cotton, lettuce, sunflower, brassicas, canola, oilseed rape, broccoli, alfalfa, and poplar.

9. A plant according to claim 1, wherein said modified FT polynucleotide is a modified endogenous polynucleotide.

10. A plant according to claim 1, wherein said modified FT polynucleotide is a modified exogenous polynucleotide.

11. Plant tissue or harvestable material derived from a plant according to claim 1.

12. An isolated FT nucleic acid, said nucleic acid encoding a modified polypeptide comprising an amino acid modification wherein said modification results in an altered phenotype, when said nucleic acid is introduced in a plant wherein said phenotypes is increased flowering and increased fruit and/or seed production; and wherein said modification comprises or consists of an amino acid substitution in SEQ ID NO: 2 at V70 and/or an amino acid substitution at T27.

13. An isolated nucleic acid according to claim 12 wherein the amino acid is substituted with A.

14. A vector comprising an isolated FT nucleic acid as defined in claim 12.

15. A plant comprising a nucleic acid as defined in claim 12 or a vector as defined in claim 14.

* * * * *

SEQUENCE LISTING

<160> NUMBER OF SEQ ID NOS: 105

<210> SEQ ID NO 1
<211> LENGTH: 528
<212> TYPE: DNA
<213> ORGANISM: Arabidopsis thaliana

<400> SEQUENCE: 1

```
atgtctataa atataagaga ccctcttata gtaagcagag ttgttggaga cgttcttgat      60
ccgtttaata gatcaatcac tctaaaggtt acttatggcc aaagagaggt gactaatggc     120
ttggatctaa ggccttctca ggttcaaaac aagccaagag ttgagattgg tggagaagac     180
ctcaggaact tctatacttt ggttatggtg gatccagatg ttccaagtcc tagcaaccct     240
```

-continued

```
cacctccgag aatatctcca ttggttggtg actgatatcc ctgctacaac tggaacaacc    300
tttggcaatg agattgtgtg ttacgaaaat ccaagtccca ctgcaggaat tcatcgtgtc    360
gtgtttatat tgtttcgaca gcttggcagg caaacagtgt atgcaccagg gtggcgccag    420
aacttcaaca ctcgcgagtt tgctgagatc tacaatctcg ccttcccgt ggccgcagtt     480 ttctacaatt gtcagaggga gagtggctgc ggaggaagaa gactttag                 528
```

<210> SEQ ID NO 2
<211> LENGTH: 175
<212> TYPE: PRT
<213> ORGANISM: Arabidopsis thaliana

<400> SEQUENCE: 2

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 3
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTV68A

<400> SEQUENCE: 3

Met Ala Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

```
Thr Gly Thr Thr Phe Gly Asn Glu Ile Val Cys Tyr Glu Asn Pro Ser
                100                 105                 110

Pro Thr Ala Gly Ile His Arg Val Val Phe Ile Leu Phe Arg Gln Leu
            115                 120                 125

Gly Arg Gln Thr Val Tyr Ala Pro Gly Trp Arg Gln Asn Phe Asn Thr
        130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 4
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTP72A

<400> SEQUENCE: 4

Met Ala Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
                100                 105                 110

Pro Thr Ala Gly Ile His Arg Val Val Phe Ile Leu Phe Arg Gln Leu
            115                 120                 125

Gly Arg Gln Thr Val Tyr Ala Pro Gly Trp Arg Gln Asn Phe Asn Thr
        130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 5
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTP77A

<400> SEQUENCE: 5

Met Ala Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45
```

```
Gln Asn Lys Pro Arg Val Glu Ile Gly Gly Glu Asp Leu Arg Asn Phe
        50                  55                  60

Tyr Thr Leu Val Met Val Asp Pro Asp Val Pro Ser Pro Ser Asn Pro
 65                  70                  75                  80

His Leu Arg Glu Tyr Leu His Trp Leu Val Thr Asp Ile Pro Ala Thr
                 85                  90                  95

Thr Gly Thr Thr Phe Gly Asn Glu Ile Val Cys Tyr Glu Asn Pro Ser
                100                 105                 110

Pro Thr Ala Gly Ile His Arg Val Val Phe Ile Leu Phe Arg Gln Leu
            115                 120                 125

Gly Arg Gln Thr Val Tyr Ala Pro Gly Trp Arg Gln Asn Phe Asn Thr
        130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175
```

<210> SEQ ID NO 6
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTG172A

<400> SEQUENCE: 6

```
Met Ala Ile Asn Ile Arg Asp Pro Leu Ile Val Ser Arg Val Val Gly
  1               5                  10                  15

Asp Val Leu Asp Pro Phe Asn Arg Ser Ile Thr Leu Lys Val Thr Tyr
                 20                  25                  30

Gly Gln Arg Glu Val Thr Asn Gly Leu Asp Leu Arg Pro Ser Gln Val
             35                  40                  45

Gln Asn Lys Pro Arg Val Glu Ile Gly Gly Glu Asp Leu Arg Asn Phe
        50                  55                  60

Tyr Thr Leu Val Met Val Asp Pro Asp Val Pro Ser Pro Ser Asn Pro
 65                  70                  75                  80

His Leu Arg Glu Tyr Leu His Trp Leu Val Thr Asp Ile Pro Ala Thr
                 85                  90                  95

Thr Gly Thr Thr Phe Gly Asn Glu Ile Val Cys Tyr Glu Asn Pro Ser
                100                 105                 110

Pro Thr Ala Gly Ile His Arg Val Val Phe Ile Leu Phe Arg Gln Leu
            115                 120                 125

Gly Arg Gln Thr Val Tyr Ala Pro Gly Trp Arg Gln Asn Phe Asn Thr
        130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175
```

<210> SEQ ID NO 7
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTR174A

<400> SEQUENCE: 7

```
Met Ala Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 8
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTS2A

<400> SEQUENCE: 8

Met Ala Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175
```

```
<210> SEQ ID NO 9
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTI5A

<400> SEQUENCE: 9

Met Ser Ile Asn Ala Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 10
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTI5A

<400> SEQUENCE: 10

Met Ser Ile Asn Ile Ala Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
```

```
                    130             135             140
Arg Glu Phe Ala Glu Ile Tyr Asn Leu Gly Leu Pro Val Ala Ala Val
145                 150             155                 160

Phe Tyr Asn Cys Gln Arg Glu Ser Gly Cys Gly Arg Arg Leu
                165             170             175

<210> SEQ ID NO 11
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTP8A

<400> SEQUENCE: 11

Met Ser Ile Asn Ile Arg Asp Ala Leu Ile Val Ser Arg Val Val Gly
1               5                   10                  15

Asp Val Leu Asp Pro Phe Asn Arg Ser Ile Thr Leu Lys Val Thr Tyr
                20                  25                  30

Gly Gln Arg Glu Val Thr Asn Gly Leu Asp Leu Arg Pro Ser Gln Val
            35                  40                  45

Gln Asn Lys Pro Arg Val Glu Ile Gly Gly Glu Asp Leu Arg Asn Phe
50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
                100                 105                 110

Pro Thr Ala Gly Ile His Arg Val Val Phe Ile Leu Phe Arg Gln Leu
            115                 120                 125

Gly Arg Gln Thr Val Tyr Ala Pro Gly Trp Arg Gln Asn Phe Asn Thr
        130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Arg Arg Leu
                165                 170                 175

<210> SEQ ID NO 12
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTV11A

<400> SEQUENCE: 12

Met Ser Ile Asn Ile Arg Asp Pro Leu Ile Ala Ser Arg Val Val Gly
1               5                   10                  15

Asp Val Leu Asp Pro Phe Asn Arg Ser Ile Thr Leu Lys Val Thr Tyr
                20                  25                  30

Gly Gln Arg Glu Val Thr Asn Gly Leu Asp Leu Arg Pro Ser Gln Val
            35                  40                  45

Gln Asn Lys Pro Arg Val Glu Ile Gly Gly Glu Asp Leu Arg Asn Phe
50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
```

```
                    85                  90                  95

Thr Gly Thr Thr Phe Gly Asn Glu Ile Val Cys Tyr Glu Asn Pro Ser
                   100                 105                 110

Pro Thr Ala Gly Ile His Arg Val Val Phe Ile Leu Phe Arg Gln Leu
               115                 120                 125

Gly Arg Gln Thr Val Tyr Ala Pro Gly Trp Arg Gln Asn Phe Asn Thr
           130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 13
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTS12A

<400> SEQUENCE: 13

Met Ser Ile Asn Ile Arg Asp Pro Leu Ile Val Ala Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
                   100                 105                 110

Pro Thr Ala Gly Ile His Arg Val Val Phe Ile Leu Phe Arg Gln Leu
               115                 120                 125

Gly Arg Gln Thr Val Tyr Ala Pro Gly Trp Arg Gln Asn Phe Asn Thr
           130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 14
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTR13A

<400> SEQUENCE: 14

Met Ser Ile Asn Ile Arg Asp Pro Leu Ile Val Ser Ala Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
```

```
                35                  40                  45
Gln Asn Lys Pro Arg Val Glu Ile Gly Gly Glu Asp Leu Arg Asn Phe
 50                  55                  60

Tyr Thr Leu Val Met Val Asp Pro Asp Val Pro Ser Pro Ser Asn Pro
 65                  70                  75                  80

His Leu Arg Glu Tyr Leu His Trp Leu Val Thr Asp Ile Pro Ala Thr
                 85                  90                  95

Thr Gly Thr Thr Phe Gly Asn Glu Ile Val Cys Tyr Glu Asn Pro Ser
                100                 105                 110

Pro Thr Ala Gly Ile His Arg Val Val Phe Ile Leu Phe Arg Gln Leu
                115                 120                 125

Gly Arg Gln Thr Val Tyr Ala Pro Gly Trp Arg Gln Asn Phe Asn Thr
            130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 15
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTD20A

<400> SEQUENCE: 15

Met Ser Ile Asn Ile Arg Asp Pro Leu Ile Val Ser Arg Val Val Gly
 1               5                  10                  15

Asp Val Leu Ala Pro Phe Asn Arg Ser Ile Thr Leu Lys Val Thr Tyr
                20                  25                  30

Gly Gln Arg Glu Val Thr Asn Gly Leu Asp Leu Arg Pro Ser Gln Val
            35                  40                  45

Gln Asn Lys Pro Arg Val Glu Ile Gly Gly Glu Asp Leu Arg Asn Phe
 50                  55                  60

Tyr Thr Leu Val Met Val Asp Pro Asp Val Pro Ser Pro Ser Asn Pro
 65                  70                  75                  80

His Leu Arg Glu Tyr Leu His Trp Leu Val Thr Asp Ile Pro Ala Thr
                 85                  90                  95

Thr Gly Thr Thr Phe Gly Asn Glu Ile Val Cys Tyr Glu Asn Pro Ser
                100                 105                 110

Pro Thr Ala Gly Ile His Arg Val Val Phe Ile Leu Phe Arg Gln Leu
                115                 120                 125

Gly Arg Gln Thr Val Tyr Ala Pro Gly Trp Arg Gln Asn Phe Asn Thr
            130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 16
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTP21A
```

<400> SEQUENCE: 16

```
Met Ser Ile Asn Ile Arg Asp Pro Leu Ile Val Ser Arg Val Val Gly
1               5                   10                  15

Asp Val Leu Asp Ala Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175
```

<210> SEQ ID NO 17
<211> LENGTH: 175
<212> TYPE: PRT
<213> ORGANISM: Artificial Sequence
<220> FEATURE:
<223> OTHER INFORMATION: Description of Artificial Sequence: Synthetic Arabidopsis thaliana FT polypeptide FTN23A

<400> SEQUENCE: 17

```
Met Ser Ile Asn Ile Arg Asp Pro Leu Ile Val Ser Arg Val Val Gly
1               5                   10                  15

Asp Val Leu Asp Pro Phe Ala Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175
```

<210> SEQ ID NO 18
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTR24A

<400> SEQUENCE: 18

Met Ser Ile Asn Ile Arg Asp Pro Leu Ile Val Ser Arg Val Val Gly
1               5                   10                  15

Asp Val Leu Asp Pro Phe Asn Ala Ser Ile Thr Leu Lys Val Thr Tyr
                20                  25                  30

Gly Gln Arg Glu Val Thr Asn Gly Leu Asp Leu Arg Pro Ser Gln Val
            35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
                100                 105                 110

Pro Thr Ala Gly Ile His Arg Val Val Phe Ile Leu Phe Arg Gln Leu
            115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Arg Arg Leu
                165                 170                 175

<210> SEQ ID NO 19
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTS25A

<400> SEQUENCE: 19

Met Ser Ile Asn Ile Arg Asp Pro Leu Ile Val Ser Arg Val Val Gly
1               5                   10                  15

Asp Val Leu Asp Pro Phe Asn Arg Ala Ile Thr Leu Lys Val Thr Tyr
                20                  25                  30

Gly Gln Arg Glu Val Thr Asn Gly Leu Asp Leu Arg Pro Ser Gln Val
            35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
                100                 105                 110

Pro Thr Ala Gly Ile His Arg Val Val Phe Ile Leu Phe Arg Gln Leu
            115                 120                 125

Gly Arg Gln Thr Val Tyr Ala Pro Gly Trp Arg Gln Asn Phe Asn Thr
            130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 20
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTI26A

<400> SEQUENCE: 20

Met Ser Ile Asn Ile Arg Asp Pro Leu Ile Val Ser Arg Val Val Gly
1               5                   10                  15

Asp Val Leu Asp Pro Phe Asn Arg Ser Ala Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 21
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTL28A

<400> SEQUENCE: 21

Met Ser Ile Asn Ile Arg Asp Pro Leu Ile Val Ser Arg Val Val Gly
1               5                   10                  15

Asp Val Leu Asp Pro Phe Asn Arg Ser Ile Thr Ala Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

```
His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 22
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTT31A

<400> SEQUENCE: 22

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Ala Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 23
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTG16A

<400> SEQUENCE: 23

Met Ser Ile Asn Ile Arg Asp Pro Leu Ile Val Ser Arg Val Val Ala
1               5                   10                  15

Asp Val Leu Asp Pro Phe Asn Arg Ser Ile Thr Leu Lys Val Thr Tyr
            20                  25                  30
```

```
Gly Gln Arg Glu Val Thr Asn Gly Leu Asp Leu Arg Pro Ser Gln Val
            35                   40                  45

Gln Asn Lys Pro Arg Val Glu Ile Gly Gly Glu Asp Leu Arg Asn Phe
 50                      55                  60

Tyr Thr Leu Val Met Val Asp Pro Asp Val Pro Ser Pro Ser Asn Pro
 65                  70                  75                  80

His Leu Arg Glu Tyr Leu His Trp Leu Val Thr Asp Ile Pro Ala Thr
                 85                  90                  95

Thr Gly Thr Thr Phe Gly Asn Glu Ile Val Cys Tyr Glu Asn Pro Ser
                100                 105                 110

Pro Thr Ala Gly Ile His Arg Val Val Phe Ile Leu Phe Arg Gln Leu
            115                 120                 125

Gly Arg Gln Thr Val Tyr Ala Pro Gly Trp Arg Gln Asn Phe Asn Thr
        130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 24
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTL19A

<400> SEQUENCE: 24

Met Ser Ile Asn Ile Arg Asp Pro Leu Ile Val Ser Arg Val Val Gly
 1               5                  10                  15

Asp Val Ala Asp Pro Phe Asn Arg Ser Ile Thr Leu Lys Val Thr Tyr
             20                  25                  30

Gly Gln Arg Glu Val Thr Asn Gly Leu Asp Leu Arg Pro Ser Gln Val
            35                   40                  45

Gln Asn Lys Pro Arg Val Glu Ile Gly Gly Glu Asp Leu Arg Asn Phe
 50                      55                  60

Tyr Thr Leu Val Met Val Asp Pro Asp Val Pro Ser Pro Ser Asn Pro
 65                  70                  75                  80

His Leu Arg Glu Tyr Leu His Trp Leu Val Thr Asp Ile Pro Ala Thr
                 85                  90                  95

Thr Gly Thr Thr Phe Gly Asn Glu Ile Val Cys Tyr Glu Asn Pro Ser
                100                 105                 110

Pro Thr Ala Gly Ile His Arg Val Val Phe Ile Leu Phe Arg Gln Leu
            115                 120                 125

Gly Arg Gln Thr Val Tyr Ala Pro Gly Trp Arg Gln Asn Phe Asn Thr
        130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 25
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTF22A
```

<400> SEQUENCE: 25

Met Ser Ile Asn Ile Arg Asp Pro Leu Ile Val Ser Arg Val Val Gly
1               5                   10                  15

Asp Val Leu Asp Pro Ala Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 26
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTK29A

<400> SEQUENCE: 26

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Ala Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 27
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTV30A

<400> SEQUENCE: 27

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Ala Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 28
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTL67A

<400> SEQUENCE: 28

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Ala Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

```
Gly Arg Gln Thr Val Tyr Ala Pro Gly Trp Arg Gln Asn Phe Asn Thr
        130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 29
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTS78A

<400> SEQUENCE: 29

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ala Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 30
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTQ140A

<400> SEQUENCE: 30

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80
```

```
His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Ala Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 31
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTI3A

<400> SEQUENCE: 31

Met Ser Ala Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 32
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTN4A

<400> SEQUENCE: 32

Met Ser Ile Ala Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30
```

-continued

Gly Gln Arg Glu Val Thr Asn Gly Leu Asp Leu Arg Pro Ser Gln Val
            35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 33
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTD7A

<400> SEQUENCE: 33

Met Ser Ile Asn Ile Arg Ala Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
            35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 34
<211> LENGTH: 175
<212> TYPE: PRT
<213> ORGANISM: Artificial Sequence
<220> FEATURE:
<223> OTHER INFORMATION: Description of Artificial Sequence: Synthetic Arabidopsis thaliana FT polypeptide FTL9A

<400> SEQUENCE: 34

```
Met Ser Ile Asn Ile Arg Asp Pro Ala Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175
```

<210> SEQ ID NO 35
<211> LENGTH: 175
<212> TYPE: PRT
<213> ORGANISM: Artificial Sequence
<220> FEATURE:
<223> OTHER INFORMATION: Description of Artificial Sequence: Synthetic Arabidopsis thaliana FT polypeptide FTV14A

<400> SEQUENCE: 35

```
Met Ser Ile Asn Ile Arg Asp Pro Leu Ile Val Ser Arg Ala Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
```

<210> SEQ ID NO 36
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTV15A

<400> SEQUENCE: 36

Met Ser Ile Asn Ile Arg Asp Pro Leu Ile Val Ser Arg Val Ala Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 37
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTD17A

<400> SEQUENCE: 37

Met Ser Ile Asn Ile Arg Asp Pro Leu Ile Val Ser Arg Val Val Gly
1               5                   10                  15

Ala Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu

```
            115                 120                 125
Gly Arg Gln Thr Val Tyr Ala Pro Gly Trp Arg Gln Asn Phe Asn Thr
        130                 135                 140
Arg Glu Phe Ala Glu Ile Tyr Asn Leu Gly Leu Pro Val Ala Ala Val
145                 150                 155                 160
Phe Tyr Asn Cys Gln Arg Glu Ser Gly Cys Gly Gly Arg Arg Leu
                165                 170                 175
```

<210> SEQ ID NO 38
<211> LENGTH: 175
<212> TYPE: PRT
<213> ORGANISM: Artificial Sequence
<220> FEATURE:
<223> OTHER INFORMATION: Description of Artificial Sequence: Synthetic
    Arabidopsis thaliana FT polypeptide FTV18A

<400> SEQUENCE: 38

```
Met Ser Ile Asn Ile Arg Asp Pro Leu Ile Val Ser Arg Val Val Gly
1               5                  10                  15
Asp Ala Leu Asp Pro Phe Asn Arg Ser Ile Thr Leu Lys Val Thr Tyr
            20                  25                  30
Gly Gln Arg Glu Val Thr Asn Gly Leu Asp Leu Arg Pro Ser Gln Val
        35                  40                  45
Gln Asn Lys Pro Arg Val Glu Ile Gly Gly Glu Asp Leu Arg Asn Phe
    50                  55                  60
Tyr Thr Leu Val Met Val Asp Pro Asp Val Pro Ser Pro Ser Asn Pro
65                  70                  75                  80
His Leu Arg Glu Tyr Leu His Trp Leu Val Thr Asp Ile Pro Ala Thr
                85                  90                  95
Thr Gly Thr Thr Phe Gly Asn Glu Ile Val Cys Tyr Glu Asn Pro Ser
            100                 105                 110
Pro Thr Ala Gly Ile His Arg Val Val Phe Ile Leu Phe Arg Gln Leu
        115                 120                 125
Gly Arg Gln Thr Val Tyr Ala Pro Gly Trp Arg Gln Asn Phe Asn Thr
    130                 135                 140
Arg Glu Phe Ala Glu Ile Tyr Asn Leu Gly Leu Pro Val Ala Ala Val
145                 150                 155                 160
Phe Tyr Asn Cys Gln Arg Glu Ser Gly Cys Gly Gly Arg Arg Leu
                165                 170                 175
```

<210> SEQ ID NO 39
<211> LENGTH: 175
<212> TYPE: PRT
<213> ORGANISM: Artificial Sequence
<220> FEATURE:
<223> OTHER INFORMATION: Description of Artificial Sequence: Synthetic
    Arabidopsis thaliana FT polypeptide FTD71A

<400> SEQUENCE: 39

```
Met Ser Ile Asn Ile Arg Asp Pro Leu Ile Val Ser Arg Val Val Gly
1               5                  10                  15
Asp Val Leu Asp Pro Phe Asn Arg Ser Ile Thr Leu Lys Val Thr Tyr
            20                  25                  30
Gly Gln Arg Glu Val Thr Asn Gly Leu Asp Leu Arg Pro Ser Gln Val
        35                  40                  45
Gln Asn Lys Pro Arg Val Glu Ile Gly Gly Glu Asp Leu Arg Asn Phe
    50                  55                  60
Tyr Thr Leu Val Met Val Ala Pro Asp Val Pro Ser Pro Ser Asn Pro
```

```
                65                  70                  75                  80
His Leu Arg Glu Tyr Leu His Trp Leu Val Thr Asp Ile Pro Ala Thr
                    85                  90                  95

Thr Gly Thr Thr Phe Gly Asn Glu Ile Val Cys Tyr Glu Asn Pro Ser
                100                 105                 110

Pro Thr Ala Gly Ile His Arg Val Val Phe Ile Leu Phe Arg Gln Leu
            115                 120                 125

Gly Arg Gln Thr Val Tyr Ala Pro Gly Trp Arg Gln Asn Phe Asn Thr
        130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 40
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTY85A

<400> SEQUENCE: 40

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Ala Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 41
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTD73A

<400> SEQUENCE: 41

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
```

```
                   20                  25                  30

Gly Gln Arg Glu Val Thr Asn Gly Leu Asp Leu Arg Pro Ser Gln Val
             35                  40                  45

Gln Asn Lys Pro Arg Val Glu Ile Gly Gly Glu Asp Leu Arg Asn Phe
         50                  55                  60

Tyr Thr Leu Val Met Val Asp Pro Ala Val Pro Ser Pro Ser Asn Pro
 65                  70                  75                  80

His Leu Arg Glu Tyr Leu His Trp Leu Val Thr Asp Ile Pro Ala Thr
                 85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 42
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTR119A

<400> SEQUENCE: 42

Met Ser Ile Asn Ile Arg Asp Pro Leu Ile Val Ser Arg Val Val Gly
  1               5                  10                  15

Asp Val Leu Asp Pro Phe Asn Arg Ser Ile Thr Leu Lys Val Thr Tyr
             20                  25                  30

Gly Gln Arg Glu Val Thr Asn Gly Leu Asp Leu Arg Pro Ser Gln Val
         35                  40                  45

Gln Asn Lys Pro Arg Val Glu Ile Gly Gly Glu Asp Leu Arg Asn Phe
     50                  55                  60

Tyr Thr Leu Val Met Val Asp Pro Asp Val Pro Ser Pro Ser Asn Pro
 65                  70                  75                  80

His Leu Arg Glu Tyr Leu His Trp Leu Val Thr Asp Ile Pro Ala Thr
                 85                  90                  95

Thr Gly Thr Thr Phe Gly Asn Glu Ile Val Cys Tyr Glu Asn Pro Ser
            100                 105                 110

Pro Thr Ala Gly Ile His Ala Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 43
<211> LENGTH: 175
<212> TYPE: PRT
<213> ORGANISM: Artificial Sequence
<220> FEATURE:
```

<223> OTHER INFORMATION: Description of Artificial Sequence: Synthetic
     Arabidopsis thaliana FT polypeptide FTR173A

<400> SEQUENCE: 43

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Ala Arg Leu
                165                 170                 175

<210> SEQ ID NO 44
<211> LENGTH: 175
<212> TYPE: PRT
<213> ORGANISM: Artificial Sequence
<220> FEATURE:
<223> OTHER INFORMATION: Description of Artificial Sequence: Synthetic
     Arabidopsis thaliana FT polypeptide FTV70A

<400> SEQUENCE: 44

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Ala Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

```
Phe Tyr Asn Cys Gln Arg Glu Ser Gly Cys Gly Gly Arg Arg Leu
            165                 170                 175
```

<210> SEQ ID NO 45
<211> LENGTH: 175
<212> TYPE: PRT
<213> ORGANISM: Artificial Sequence
<220> FEATURE:
<223> OTHER INFORMATION: Description of Artificial Sequence: Synthetic
      Arabidopsis thaliana FT polypeptide FTT27A

<400> SEQUENCE: 45

```
Met Ser Ile Asn Ile Arg Asp Pro Leu Ile Val Ser Arg Val Val Gly
  1               5                  10                  15

Asp Val Leu Asp Pro Phe Asn Arg Ser Ile Ala Leu Lys Val Thr Tyr
                 20                  25                  30

Gly Gln Arg Glu Val Thr Asn Gly Leu Asp Leu Arg Pro Ser Gln Val
             35                  40                  45

Gln Asn Lys Pro Arg Val Glu Ile Gly Gly Glu Asp Leu Arg Asn Phe
         50                  55                  60

Tyr Thr Leu Val Met Val Asp Pro Asp Val Pro Ser Pro Ser Asn Pro
 65                  70                  75                  80

His Leu Arg Glu Tyr Leu His Trp Leu Val Thr Asp Ile Pro Ala Thr
                 85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175
```

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      HvHygF3 primer

<400> SEQUENCE: 46
ggatttcggc tccaacaatg                                                20

<210> SEQ ID NO 47
<211> LENGTH: 21
<212> TYPE: DNA
<213> ORGANISM: Artificial Sequence
    <220> FEATURE:
<223> OTHER INFORMATION: Description of Artificial Sequence: Synthetic
      HvHygR2 primer

<400> SEQUENCE: 47
tattgggaat ccccgaacat c                                              21

<210> SEQ ID NO 48
<211> LENGTH: 20
<212> TYPE: DNA
<213> ORGANISM: Artificial Sequence
<220> FEATURE:

```
<223> OTHER INFORMATION: Description of Artificial Sequence: Synthetic
      HvCon2F1 primer

<400> SEQUENCE: 48
tgctaaccgt gtggcatcac                                                    20

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      HvCon2R1 primer

<400> SEQUENCE: 49
ggtacatagt gctgctgcat ctg                                                23

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      HvHygP primer
<220> FEATURE:
<223> OTHER INFORMATION: 5'-Fam dye
<220> FEATURE:
<223> OTHER INFORMATION: 3'-Tamra dye

<400> SEQUENCE: 50
cagcggtcat tgactggagc gagg                                               24

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      HvCon2P primer
<220> FEATURE:
<223> OTHER INFORMATION: 5'-VIC dye
<220> FEATURE:
<223> OTHER INFORMATION: 3'-Tamra dye

<400> SEQUENCE: 51
catgagcgtg tgcgtgtctg cg                                                 22

<210> SEQ ID NO 52
<211> LENGTH: 35
<212> TYPE: DNA
<213> ORGANISM: Artificial Sequence
<220> FEATURE:
<223> OTHER INFORMATION: Description of Artificial Sequence: Synthetic
      PP331 primer

<400> SEQUENCE: 52
aagatcatcg atgtctataa atataagaga ccctc                                   35

<210> SEQ ID NO 53
<211> LENGTH: 35
<212> TYPE: DNA
<213> ORGANISM: Artificial Sequence
<220> FEATURE:
<223> OTHER INFORMATION: Description of Artificial Sequence: Synthetic
      PP332 primer

<400> SEQUENCE: 53
agaagccggc cgaagtcttc ttcctccgca gccac                                   35
```

```
<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      PP527 primer

<400> SEQUENCE: 54
tctggatcca ccataaccgc agtatagaag                                      30

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      PP528 primer

<400> SEQUENCE: 55
cttctatact gcggttatgg tggatccaga                                      30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      PP529 primer

<400> SEQUENCE: 56
tctggatcca ccatcgccaa agtatagaag                                      30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      PP530 primer

<400> SEQUENCE: 57
cttctatact ttggcgatgg tggatccaga                                      30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      PP531 primer

<400> SEQUENCE: 58
tctggatccg ccataaccaa agtatagaag                                      30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      PP532 primer

<400> SEQUENCE: 59
cttctatact ttggttatgg cggatccaga                                      30
```

```
<210> SEQ ID NO 60
<211> LENGTH: 32
<212> TYPE: DNA
<213> ORGANISM: Artificial Sequence
<220> FEATURE:
<223> OTHER INFORMATION: Description of Artificial Sequence: Synthetic
      PP533 primer

<400> SEQUENCE: 60
acttggaaca tctggcgcca ccataaccaa ag                                  32

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: Synthetic
      PP534 primer

<400> SEQUENCE: 61
ctttggttat ggtggcgcca gatgttccaa gt                                  32

<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence: Synthetic
      PP535 primer

<400> SEQUENCE: 62
acttggaaca tccgcatcca ccataaccaa ag                                  32

<210> SEQ ID NO 63
<211> LENGTH: 32
<212> TYPE: DNA
<213> ORGANISM: Artificial Sequence
<220> FEATURE:
<223> OTHER INFORMATION: Description of Artificial Sequence: Synthetic
      PP536 primer

<400> SEQUENCE: 63
ctttggttat ggtggatgcg gatgttccaa gt                                  32

<210> SEQ ID NO 64
<211> LENGTH: 32
<212> TYPE: DNA
<213> ORGANISM: Artificial Sequence
<220> FEATURE:
<223> OTHER INFORMATION: Description of Artificial Sequence: Synthetic
      PP537 primer

<400> SEQUENCE: 64
acttggaacc gctggatcca ccataaccaa ag                                  32

<210> SEQ ID NO 65
<211> LENGTH: 32
<212> TYPE: DNA
<213> ORGANISM: Artificial Sequence
<220> FEATURE:
<223> OTHER INFORMATION: Description of Artificial Sequence: Synthetic
      PP538 primer

<400> SEQUENCE: 65
ctttggttat ggtggatcca gcggttccaa gt                                  32
```

```
<210> SEQ ID NO 66
<211> LENGTH: 32
<212> TYPE: DNA
<213> ORGANISM: Artificial Sequence
<220> FEATURE:
<223> OTHER INFORMATION: Description of Artificial Sequence: Synthetic
      PP539 primer

<400> SEQUENCE: 66
ctcggaggtg agggttgctc gcacttggaa ca                                      32

<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence: Synthetic
      PP540 primer

<400> SEQUENCE: 67
tgttccaagt gcgagcaacc ctcacctccg ag                                      32

<210> SEQ ID NO 68
<211> LENGTH: 32
<212> TYPE: DNA
<213> ORGANISM: Artificial Sequence
<220> FEATURE:
<223> OTHER INFORMATION: Description of Artificial Sequence: Synthetic
      PP541 primer

<400> SEQUENCE: 68
ctcggaggtg agggttcgca ggacttggaa ca                                      32

<210> SEQ ID NO 69
<211> LENGTH: 32
<212> TYPE: DNA
<213> ORGANISM: Artificial Sequence
<220> FEATURE:
<223> OTHER INFORMATION: Description of Artificial Sequence: Synthetic
      PP542 primer

<400> SEQUENCE: 69
tgttccaagt cctgcgaacc ctcacctccg ag                                      32

<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence: Synthetic
      PP543 primer

<400> SEQUENCE: 70
accaaccaat ggagcgcttc tcggaggtga g                                       31

<210> SEQ ID NO 71
<211> LENGTH: 31
<212> TYPE: DNA
<213> ORGANISM: Artificial Sequence
<220> FEATURE:
<223> OTHER INFORMATION: Description of Artificial Sequence: Synthetic
      PP544 primer

<400> SEQUENCE: 71
ctcacctccg agaagcgctc cattggttgg t                                       31

<210> SEQ ID NO 72
```

```
<211> LENGTH: 31
<212> TYPE: DNA
<213> ORGANISM: Artificial Sequence
<220> FEATURE:
<223> OTHER INFORMATION: Description of Artificial Sequence: Synthetic
      PP545 primer

<400> SEQUENCE: 72
tataaacacg accgcatgaa ttcctgcagt g                                    31

<210> SEQ ID NO 73
<211> LENGTH: 31
<212> TYPE: DNA
<213> ORGANISM: Artificial Sequence
<220> FEATURE:
<223> OTHER INFORMATION: Description of Artificial Sequence: Synthetic
      PP546 primer

<400> SEQUENCE: 73
cactgcagga attcatgcgg tcgtgtttat a                                    31

<210> SEQ ID NO 74
<211> LENGTH: 32
<212> TYPE: DNA
<213> ORGANISM: Artificial Sequence
<220> FEATURE:
<223> OTHER INFORMATION: Description of Artificial Sequence: Synthetic
      PP547 primer

<400> SEQUENCE: 74
tgttgaagtt cgcgcgccac cctggtgcat ac                                   32

<210> SEQ ID NO 75
<211> LENGTH: 32
<212> TYPE: DNA
<213> ORGANISM: Artificial Sequence
<220> FEATURE:
<223> OTHER INFORMATION: Description of Artificial Sequence: Synthetic
      PP548 primer

<400> SEQUENCE: 75
gtatgcacca gggtggcgcg cgaacttcaa ca                                   32

<210> SEQ ID NO 76
<211> LENGTH: 35
<212> TYPE: DNA
<213> ORGANISM: Artificial Sequence
<220> FEATURE:
<223> OTHER INFORMATION: Description of Artificial Sequence: Synthetic
      PP549 primer

<400> SEQUENCE: 76
ggaagacggc cgctaaagtc ttctcgctcc gcagc                                35

<210> SEQ ID NO 77
<211> LENGTH: 35
<212> TYPE: DNA
<213> ORGANISM: Artificial Sequence
<220> FEATURE:
<223> OTHER INFORMATION: Description of Artificial Sequence: Synthetic
      PP551 primer

<400> SEQUENCE: 77
ggaagacggc cgctaaagtc tcgctcctcc gcagc                                35

<210> SEQ ID NO 78
<211> LENGTH: 35
```

<210> SEQ ID NO 79
<211> LENGTH: 22
<212> TYPE: PRT
<213> ORGANISM: Artificial Sequence
<220> FEATURE:
<223> OTHER INFORMATION: Description of Artificial Sequence: Synthetic
      PP552 primer

<400> SEQUENCE: 78
ggaagacggc cgctaaagcg ctcttcctcc gcagc                                    35

<210> SEQ ID NO 79
<211> LENGTH: 22
<212> TYPE: PRT
<213> ORGANISM: Artificial Sequence
<220> FEATURE:
<223> OTHER INFORMATION: Description of Artificial Sequence: Synthetic
      Arabidopsis thaliana PEBP domain

<400> SEQUENCE: 79

Tyr Thr Leu Val Met Val Asp Pro Asp Val Pro Ser Pro Ser Asn Pro
1               5                   10                  15

His Leu Arg Glu Tyr Leu
            20

<210> SEQ ID NO 80
<211> LENGTH: 174
<212> TYPE: PRT
<213> ORGANISM: Antirrhinum sp.

<400> SEQUENCE: 80

Met Pro Arg Asp Arg Asp Pro Leu Val Val Gly Arg Val Ile Gly Glu
1               5                   10                  15

Val Leu Glu Pro Phe Thr Arg Ser Ile Gly Leu Arg Val Ile Tyr Asn
                20                  25                  30

Asn Arg Glu Val Ser Asn Gly Cys Asp Leu Arg Pro Ser Gln Val Val
            35                  40                  45

Asn Gln Pro Arg Val Glu Ile Gly Gly Asp Asp Leu Arg Thr Phe Tyr
        50                  55                  60

Thr Leu Val Met Val Asp Pro Asp Ala Pro Ser Pro Ser Asp Pro Ser
65                  70                  75                  80

Leu Arg Glu Tyr Leu His Trp Leu Val Thr Asp Ile Pro Ala Thr Thr
                85                  90                  95

Gly Thr Asn Phe Gly Gln Glu Ile Val Cys Tyr Glu Asn Pro Arg Pro
            100                 105                 110

Ser Met Gly Ile His Arg Phe Val Phe Thr Leu Phe Arg Gln Leu Gly
        115                 120                 125

Arg Gln Thr Val Tyr Pro Pro Gly Trp Arg Gln Asn Phe Asn Thr Arg
    130                 135                 140

Asp Phe Ala Glu Leu Tyr Asn Leu Gly Ala Pro Val Ala Ala Val Tyr
145                 150                 155                 160

Phe Asn Cys Gln Arg Glu Ser Gly Thr Gly Gly Arg Arg Arg
                165                 170

<210> SEQ ID NO 81
<211> LENGTH: 177
<212> TYPE: PRT
<213> ORGANISM: Citrus sp.

<400> SEQUENCE: 81

Met Ser Ser Arg Glu Arg Asp Pro Leu Ile Val Gly Arg Val Val Gly
1               5                   10                  15

```
Asp Val Leu Asp Asn Phe Thr Arg Thr Ile Pro Met Arg Ile Thr Tyr
             20                  25                  30

Ser Asn Lys Asp Val Asn Asn Gly Arg Glu Leu Lys Pro Ser Glu Val
         35                  40                  45

Leu Asn Gln Pro Arg Ala Glu Ile Gly Gly Asp Asp Leu Arg Thr Phe
     50                  55                  60

Tyr Thr Leu Val Met Val Asp Pro Asp Ala Pro Ser Pro Ser Asp Pro
65                  70                  75                  80

Ser Leu Arg Glu Tyr Leu His Trp Leu Val Thr Asp Ile Pro Ala Thr
                 85                  90                  95

Thr Gly Ala Ser Phe Gly Gln Glu Ile Val Asn Tyr Glu Ser Pro Arg
            100                 105                 110

Pro Thr Met Gly Ile His Arg Phe Val Phe Val Leu Phe Arg Gln Leu
        115                 120                 125

Gly Arg Gln Thr Val Tyr Ala Pro Gly Trp Arg Gln Asn Phe Ser Thr
    130                 135                 140

Arg Asp Phe Ala Glu Leu Tyr Asn Leu Gly Pro Pro Val Ala Ala Val
145                 150                 155                 160

Tyr Phe Asn Cys Gln Arg Glu Ser Gly Ser Gly Gly Arg Pro Val Arg
                165                 170                 175

Arg

<210> SEQ ID NO 82
<211> LENGTH: 175
<212> TYPE: PRT
<213> ORGANISM: Lactuca sp.

<400> SEQUENCE: 82

Met Met Pro Arg Glu Arg Asp Pro Leu Val Val Gly Arg Val Ile Gly
1               5                   10                  15

Asp Val Leu Asp Ser Phe Thr Lys Ser Ile Asn Leu Ser Val Thr Tyr
             20                  25                  30

Asn Asp Arg Glu Val Ser Asn Gly Cys Glu Leu Lys Pro Ser Gln Val
         35                  40                  45

Val Asn Gln Pro Arg Val Asp Ile Gly Gly Asp Asp Leu Arg Ala Phe
     50                  55                  60

His Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Ala Thr
                 85                  90                  95

Thr Gly Ala Arg Phe Gly Gln Glu Ile Val Cys Tyr Glu Ser Pro Arg
            100                 105                 110

Pro Ser Met Gly Ile His Arg Met Val Phe Val Leu Phe Arg Gln Leu
        115                 120                 125

Gly Arg Gln Thr Val Tyr Ala Pro Gly Trp Arg Gln Asn Phe Asn Thr
    130                 135                 140

Lys Asp Phe Ala Glu Leu Tyr Asn Leu Gly Ser Pro Val Ala Ala Val
145                 150                 155                 160

Tyr Phe Asn Cys Gln Arg Glu Ser Gly Phe Gly Gly Arg Arg Arg
                165                 170                 175

<210> SEQ ID NO 83
<211> LENGTH: 174
<212> TYPE: PRT
<213> ORGANISM: Malus sp.
```

<400> SEQUENCE: 83

```
Met Pro Arg Asp Arg Asp Pro Leu Val Val Gly Arg Val Val Gly Asp
1               5                   10                  15

Val Leu Asp Pro Phe Thr Arg Ser Val Ser Leu Arg Val Thr Tyr Gly
            20                  25                  30

Thr Lys Glu Val Asn Asn Gly Cys Glu Leu Lys Pro Ser Glu Val Val
        35                  40                  45

Gln Gln Pro Arg Ala Asp Ile Gly Gly Asp Leu Arg Thr Phe Tyr
    50                  55                  60

Thr Leu Val Met Val Asp Pro Asp Ala Pro Ser Pro Ser Asp Pro Asn
65                  70                  75                  80

Leu Lys Glu Tyr Leu His Trp Leu Val Thr Asp Ile Pro Ala Thr Thr
                85                  90                  95

Ala Ala Ser Phe Gly Gln Glu Ile Val Cys Tyr Glu Ser Pro Arg Pro
            100                 105                 110

Thr Val Gly Ile His Arg Phe Val Leu Val Val Phe Arg Gln Leu Gly
            115                 120                 125

Arg Gln Thr Val Tyr Ala Pro Gly Trp Arg Gln Asn Phe Asn Thr Arg
    130                 135                 140

Asp Phe Ala Glu Leu Tyr Asn Leu Gly Leu Pro Val Ser Val Val Tyr
145                 150                 155                 160

Phe Asn Cys Gln Arg Glu Gly Gly Ser Gly Gly Arg Arg Arg
                165                 170
```

<210> SEQ ID NO 84
<211> LENGTH: 174
<212> TYPE: PRT
<213> ORGANISM: Populus sp.

<400> SEQUENCE: 84

```
Met Ser Arg Asp Arg Asp Pro Leu Ser Val Gly Arg Val Ile Gly Asp
1               5                   10                  15

Val Leu Asp Pro Phe Thr Lys Ser Ile Ser Leu Arg Val Thr Tyr Ser
            20                  25                  30

Ser Arg Glu Val Asn Asn Gly Cys Glu Leu Lys Pro Ser Gln Val Ala
        35                  40                  45

Asn Gln Pro Arg Val Asp Ile Gly Gly Glu Asp Leu Arg Thr Phe Tyr
    50                  55                  60

Thr Leu Val Met Val Asp Pro Asp Ala Pro Ser Pro Ser Asp Pro Ser
65                  70                  75                  80

Leu Arg Glu Tyr Leu His Trp Leu Val Thr Asp Ile Pro Ala Thr Thr
                85                  90                  95

Gly Ala Ser Phe Gly His Glu Thr Val Cys Tyr Glu Asn Pro Arg Pro
            100                 105                 110

Thr Met Gly Ile His Arg Phe Val Phe Val Leu Phe Arg Gln Leu Gly
            115                 120                 125

Arg Gln Thr Val Tyr Ala Pro Gly Trp Arg Gln Asn Phe Asn Thr Arg
    130                 135                 140

Asp Phe Ala Glu Val Tyr Asn Leu Gly Ser Pro Val Ala Ala Val Tyr
145                 150                 155                 160

Phe Asn Cys Gln Arg Glu Ser Gly Ser Gly Gly Arg Arg Arg
                165                 170
```

<210> SEQ ID NO 85
<211> LENGTH: 177

```
<212> TYPE: PRT
<213> ORGANISM: Triticum sp.

<400> SEQUENCE: 85

Met Ala Gly Arg Asp Arg Asp Pro Leu Val Val Gly Arg Val Val Gly
1               5                   10                  15

Asp Val Leu Asp Pro Phe Val Arg Thr Thr Asn Leu Arg Val Thr Phe
            20                  25                  30

Gly Asn Arg Thr Val Ser Asn Gly Cys Glu Leu Lys Pro Ser Met Val
        35                  40                  45

Ala Gln Gln Pro Arg Val Glu Val Gly Gly Asn Glu Met Arg Thr Phe
    50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Ala Ser Phe Gly Gln Glu Val Met Cys Tyr Glu Ser Pro Arg
            100                 105                 110

Pro Thr Met Gly Ile His Arg Phe Val Leu Val Leu Phe Gln Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Pro Val Ala Ala Val
145                 150                 155                 160

Tyr Phe Asn Cys Gln Arg Glu Ala Gly Ser Gly Gly Arg Arg Met Tyr
                165                 170                 175

Asn

<210> SEQ ID NO 86
<211> LENGTH: 174
<212> TYPE: PRT
<213> ORGANISM: Vitis sp.

<400> SEQUENCE: 86

Met Pro Arg Glu Arg Asp Pro Leu Val Val Gly Arg Val Val Gly Asp
1               5                   10                  15

Val Leu Asp Pro Phe Leu Arg Ser Ile Thr Leu Arg Val Thr Tyr Asn
            20                  25                  30

Asn Arg Glu Val Ala Asn Gly Cys Glu Phe Arg Pro Ser Gln Leu Val
        35                  40                  45

Ser Gln Pro Arg Val Asp Ile Gly Gly Asp Asp Leu Arg Thr Phe Tyr
    50                  55                  60

Thr Leu Val Met Val Asp Pro Asp Ala Pro Ser Pro Ser Asn Pro Asn
65                  70                  75                  80

Leu Arg Glu Tyr Leu His Trp Leu Val Thr Asp Ile Pro Ala Thr Thr
                85                  90                  95

Gly Ala Asn Phe Gly Gln Glu Ile Val Cys Tyr Glu Ser Pro Arg Pro
            100                 105                 110

Thr Ala Gly Ile His Arg Phe Val Phe Val Leu Phe Arg Gln Leu Gly
        115                 120                 125

Arg Gln Thr Val Tyr Ala Pro Gly Trp Arg Gln Asn Phe Asn Thr Arg
    130                 135                 140

Asp Phe Ala Glu Leu Tyr Asn Leu Gly Leu Pro Val Ala Ala Val Tyr
145                 150                 155                 160

Phe Asn Cys Gln Arg Glu Gly Gly Ser Gly Gly Arg Arg Ser
```

165        170

<210> SEQ ID NO 87
<211> LENGTH: 179
<212> TYPE: PRT
<213> ORGANISM: Oryza sp.

<400> SEQUENCE: 87

Met Ala Gly Ser Gly Arg Asp Arg Asp Pro Leu Val Val Gly Arg Val
1               5                   10                  15

Val Gly Asp Val Leu Asp Ala Phe Val Arg Ser Thr Asn Leu Lys Val
            20                  25                  30

Thr Tyr Gly Ser Lys Thr Val Ser Asn Gly Cys Glu Leu Lys Pro Ser
        35                  40                  45

Met Val Thr His Gln Pro Arg Val Glu Val Gly Gly Asn Asp Met Arg
    50                  55                  60

Thr Phe Tyr Thr Leu Val Met Val Asp Pro Asp Ala Pro Ser Pro Ser
65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser
            100                 105                 110

Pro Arg Pro Thr Met Gly Ile His Arg Leu Val Phe Val Leu Phe Gln
        115                 120                 125

Gln Leu Gly Arg Gln Thr Val Tyr Ala Pro Gly Trp Arg Gln Asn Phe
130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Val Tyr Asn

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(21)

<400> SEQUENCE: 88 atg tct ata aat ata aga gac                                          21
Met Ser Ile Asn Ile Arg Asp
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Met Ser Ile Asn Ile Arg Asp
1               5

<210> SEQ ID NO 90

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tagtctataa atataagaga c                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
atgtctataa atataagaga c                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
atgtctataa atataagaga c                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(21)

<400> SEQUENCE: 93 act ttg gtt atg gtg gat cca                                          21
Thr Leu Val Met Val Asp Pro
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Leu Val Met Val Asp Pro
1               5

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
```
actttggtta tggtggatcc a                                        21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
actttggtta tggcggatcc a                                        21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
actttggtta tggtggatcc a                                        21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(21)

<400> SEQUENCE: 98 ggc tgc gga gga aga aga ctt                                    21
Gly Cys Gly Gly Arg Arg Leu
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Cys Gly Gly Arg Arg Leu
1               5

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ggctgcggag gaagaagact t                                        21

<210> SEQ ID NO 101
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 101
ggctgcggag gaagaagact t                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ggctgcggag gagcgagact t                                              21

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tccggatagt ctataatata aga                                            23

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tccggaatgt ctataaatat aaga                                           24

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
atggcggatc cacatgttcc aagt                                           24
```